(12) United States Patent
Watanabe et al.

(10) Patent No.: US 9,103,923 B2
(45) Date of Patent: Aug. 11, 2015

(54) X-RAY IMAGING APPARATUS AND X-RAY IMAGING METHOD

(75) Inventors: Masatoshi Watanabe, Isehara (JP); Taihei Mukaide, Atsugi (JP); Kazuhiro Takada, Kawasaki (JP); Kazunori Fukuda, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 471 days.

(21) Appl. No.: 13/121,776

(22) PCT Filed: Jul. 23, 2010

(86) PCT No.: PCT/JP2010/062972
§ 371 (c)(1),
(2), (4) Date: Mar. 30, 2011

(87) PCT Pub. No.: WO2011/010750
PCT Pub. Date: Jan. 27, 2011

(65) Prior Publication Data
US 2011/0176662 A1    Jul. 21, 2011

(30) Foreign Application Priority Data

Jul. 24, 2009  (JP) ................................ 2009-173452

(51) Int. Cl.
G01T 1/202   (2006.01)
G01N 23/223  (2006.01)
G01T 1/164   (2006.01)

(52) U.S. Cl.
CPC .............. *G01T 1/202* (2013.01); *G01N 23/223* (2013.01); *G01T 1/1641* (2013.01); *G01N 2223/076* (2013.01)

(58) Field of Classification Search
CPC ........ A61B 6/484; A61B 6/485; G01N 23/02; G01N 23/04; G01N 2223/505; G01T 1/20; G01T 1/2006; G01T 1/362
USPC .............................. 378/62, 98.8; 250/370.11
See application file for complete search history.

(56) References Cited

U.S. PATENT DOCUMENTS 6,087,663 A * 7/2000 Moisan et al. ................ 250/367
2006/0202128 A1* 9/2006 Berger et al. ............ 250/370.11

FOREIGN PATENT DOCUMENTS

CN    1937960 A    3/2007
JP    11258349 A   9/1999
(Continued)

OTHER PUBLICATIONS

Translation for JP 11/258349 published Sep. 24, 1999.*
(Continued)

*Primary Examiner* — Glen Kao
(74) *Attorney, Agent, or Firm* — Canon USA Inc. IP Division

(57) ABSTRACT

An X-ray imaging apparatus and an X-ray imaging method for use in the X-ray imaging apparatus are provided. The X-ray imaging apparatus includes a separating element configured to spatially separate an X-ray generated by an X-ray generator unit and a scintillator array including a plurality of first scintillators arranged therein, where the separated X-rays are made incident on the first scintillators. Each of the first scintillators is configured to vary an intensity of fluorescence induced by the X-ray in accordance with an incident position of the X-ray. The X-ray imaging apparatus further includes a detector configured to detect the intensity of fluorescence emitted from the scintillator array.

18 Claims, 17 Drawing Sheets

(56) References Cited

FOREIGN PATENT DOCUMENTS

| JP | 2002-102215 A | 4/2002 |
|---|---|---|
| JP | 2003010162 A | 1/2003 |
| JP | 2004317299 A | 11/2004 |
| JP | 2009156740 A | 7/2009 |
| SU | 1519382 A1 | 12/1993 |
| WO | 2008/029107 A2 | 3/2008 |

OTHER PUBLICATIONS

Translation for JP 2003-010162 published Jan. 14, 2003.*
Kagoshima et al., "Scanning Differential-Phase-Contrast Hard X-Ray Microscopy with Wedge Absorber Detector", Japanese Journal of Applied Physics, Oct. 15, 2004, vol. 43, pp. L1449-L1451.
Wilkins et al.,"Phase-Contrast Imaging using Polychromatic Hard X-rays", Letters to Nature, Nov. 1996, pp. 335-338, vol. 384.

* cited by examiner

X-RAY IMAGING APPARATUS AND X-RAY IMAGING METHOD

TECHNICAL FIELD

The present invention relates to an x-ray imaging apparatus and an x-ray imaging method using X-rays.

BACKGROUND ART

A nondestructive testing technique using an X-ray has been widely used in industry to medicine. An X-ray is electromagnetic waves having a wavelength ranging from about 1 pm to 10 nm (from about $10^{-12}$ to $10^{-8}$ m). An X-ray having a short wavelength (greater than about 2 keV) is referred to as a "hard X-ray". In contrast, an X-ray having a long wavelength (ranging from about 0.1 keV to 2 keV) is referred to as a "soft X-ray".

The absorption contrast method is used for, for example, internal crack inspection of steel materials and security applications, such as baggage inspection. In contrast, for objects to be inspected having a low density, the contrast due to absorption of X-rays is negligibly small. Accordingly, for such objects, an X-ray phase imaging method in which changes in phase caused by a detection object is detected is advantageous.

One of a variety of X-ray phase imaging methods is a refraction contrast method described in PTL 1. The refraction contrast method uses a refraction effect caused by a phase shift in an X-ray induced by a detection object. In the refraction contrast method, an X-ray source having a microfocus is used, and a distance between a detection object and a detector is set to be large. Thus, an image is captured. According to a refraction contrast method, the contour of the image of the detection object is enhanced using the refraction effect of an X-ray caused by the detection object. In addition, unlike other X-ray phase imaging methods, the refraction contrast method does not necessarily require an X-ray having a high interference characteristic, such as synchrotron radiation, since the refraction contrast method uses the refraction effect.

CITATION LIST

Patent Literature

PTL 1 Japanese Patent Laid-Open No. 2002-102215

SUMMARY OF INVENTION

Technical Problem

However, in the refraction contrast method described in PTL 1, a refraction angle of an X-ray in the refraction effect caused by a detection object is significantly small. Accordingly, in order to obtain an image having an enhanced contour, the distance between the detection object and a detector needs to be sufficiently large. As a result, when the method described in PTL 1 is employed, the size of an apparatus is increased.

Accordingly, the present invention provides an x-ray imaging apparatus and an x-ray imaging method capable of solving the problem of a refraction contrast method.

Solution to Problem

According to an embodiment of the present embodiment, an X-ray imaging apparatus includes a separating element configured to spatially separate X-rays generated by an X-ray generator unit, a scintillator array including a plurality of first scintillators arranged therein, where the separated X-rays are made incident on the first scintillators, and a detector configured to detect an intensity of fluorescence emitted from the scintillator array. Each of the first scintillators is configured to have a fluorescence emission intensity gradient in which an intensity of fluorescence induced by the X-ray varies in accordance with an incident position of the X-ray.

Advantageous Effects of Invention

According to the present invention, an x-ray imaging apparatus and an x-ray imaging method capable of solving the problem of a refraction contrast method can be provided.

DESCRIPTION OF EMBODIMENTS

According to embodiments of the present invention, information regarding a change in intensity distribution or a change in position caused by a refraction effect is acquired by using a scintillator array having a plurality of scintillators having a fluorescence emission intensity gradient. As used herein, the term "scintillator having a fluorescence emission intensity gradient" refers to a scintillator in which the fluorescence emission intensity thereof changes in a continuous manner in accordance with an incident position of an X-ray (a first scintillator). Such a scintillator can be produced by making the shape thereof change in a continuous manner or in a stepwise manner. Alternatively, such a scintillator can be produced by making the fluorescence emission intensity per unit volume change in a continuous or stepwise manner. Note that, hereinafter, in some cases, the term "continuous manner" includes the meaning of "stepwise manner".

In addition, if more accurate information of phase shift is needed by taking into account the absorption by a detection object, a scintillator having a constant fluorescence emission intensity in a direction in which the incident X-ray moves (a second scintillator) may be used. Such scintillator is described in more detail below with reference to a fifth embodiment.

Alternatively, if more accurate information of phase shift is needed by taking into account the absorption by a detection object, a scintillator having a different change in the fluorescence emission intensity or a different increasing and decreasing tendency of the fluorescence emission intensity in a movement direction of the incident X-ray (a third scintillator) may be used. Such scintillator is described in more detail below with reference to a sixth embodiment.

X-ray imaging apparatuses and X-ray imaging methods according to exemplary embodiments of the present invention are described below.

First Embodiment

According to a first embodiment, an exemplary configuration of an X-ray imaging apparatus that captures an image using a phase shift in an X-ray is described.

Figure 17:
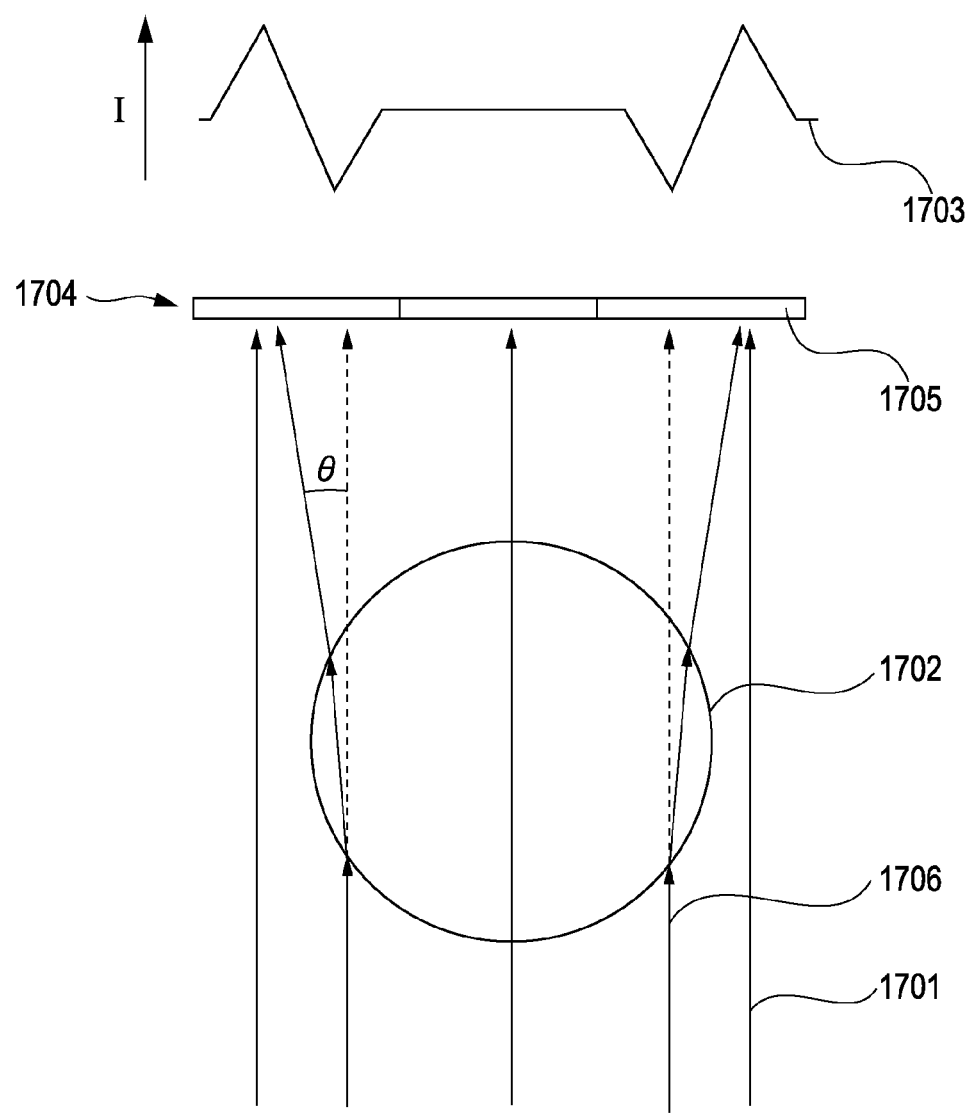
FIG. 17 is a schematic illustration of refraction of an X-ray occurring when X-rays are transmitted through a substance.

FIG. 17 is a schematic illustration of the refraction of an X-ray occurring when the X-ray is transmitted through a substance. The index of refraction of an X-ray with respect to a substance is slightly lower than 1. Accordingly, in the case shown in FIG. 17, an X-ray 1706 entering a substance 1702 at the boundary between the substance 1702 and empty space is refracted in an outward direction away from the substance 1702. At that time, the X-ray 1706 refracted at the boundary of the substance overlaps with an X-ray 1701 traveling outside the substance 1702, and the intensity of the X-ray increases on a detector 1704. In contrast, the intensity of the portion of the refracted x-ray along the extension of the incident x-rays decreases. As a result, as shown in FIG. 17, an obtained transmission X-ray intensity distribution 1703 has an enhanced contour of the substance 1702.

In this case, the angle of refraction θ of the X-ray is significantly small. Accordingly, due to the small pixel size of the detector, it is difficult to detect the enhancement of contours unless the distance between the substance and the detector is set to be large. Therefore, in the refraction contrast method described in PTL 1, a detection object and the detector are disposed so that the distance therebetween is sufficiently large in order to detect the enhancement of contours and the image is enlarged. Consequently, the size of the apparatus is increased.

That is, if the distance between a detection object and the detector is small, the size of a pixel 1705 of a detector 1704 is larger than the strong and weak pattern of the transmission X-ray intensity distribution 1703. Thus, the intensities of the strong pattern and week pattern cancel out in a pixel. Therefore, an image having an enhanced contour cannot be obtained.

Accordingly, the present embodiment employs a scintillator having a fluorescence emission intensity gradient in order to sufficiently obtain X-ray information of phase shift even when the distance between a detection object and the detector is set to be small.

Figure 1:
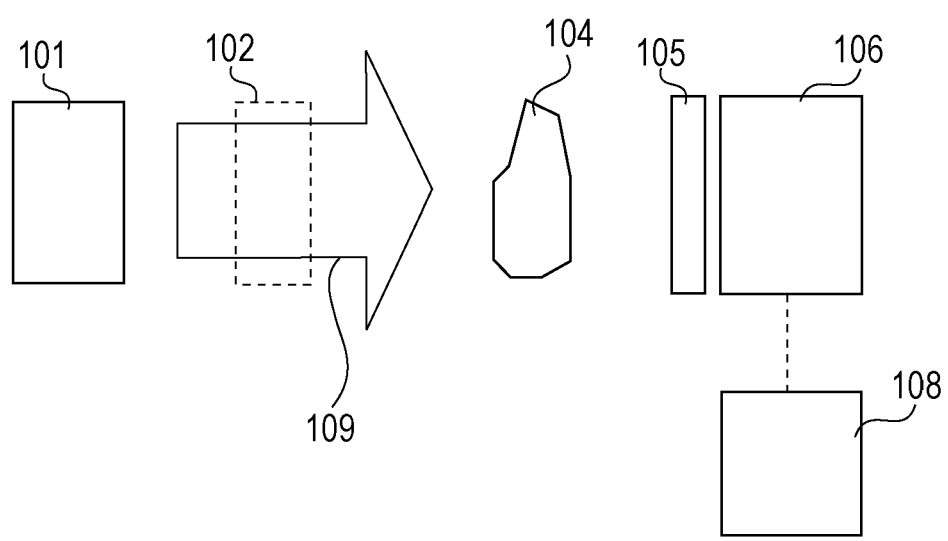
FIG. 1 illustrates an exemplary configuration of an X-ray imaging apparatus according to a first embodiment of the present invention.

FIG. 1 illustrates an exemplary configuration of an X-ray imaging apparatus according to the present embodiment.

An X-ray 109 is generated by an X-ray source 101. The phase of the X-ray is varied by a detection object 104. As a result, the X-ray is refracted. The refracted X-ray is made incident on a scintillator array 105. The scintillator array 105 generates fluorescence due to the incident X-ray. A detector 106 detects the intensity of the fluorescence emitted from each of scintillators of the scintillator array 105. The information regarding the X-ray obtained by the detector 106 is output to a display unit 108, such as a monitor.

Examples of the detection object 104 include the human body, a non-organic material, and a non-organic/organic compound material. Note that a moving unit (not shown) may be additionally provided in order to move the detection object 104. Since the detection object 104 can be appropriately moved by the moving unit, an image of desired part of the detection object 104 can be obtained.

A variety of light detector can be used as the detector 106. For example, a solid-state imaging element, such as a CCD image sensor or a CMOS image sensor using Si, is selected for ultraviolet light or visible light. In addition, a solid-state imaging element using a compound semiconductor, such as InSb or CdHgTe, is selected for infrared light. The detector 106 may be disposed so as to be close to the scintillator array 105. Alternatively, the detector 106 may be disposed so as to be spaced from the scintillator array 105 by a predetermined distance. Still alternatively, the scintillator array 105 may be integrated into the detector 106.

Note that when a monochromatic X-ray is used, a monochromating unit 102 may be disposed between the X-ray source 101 and the detection object 104. A monochromator combined with a slit or an X-ray multilayer mirror can be used as the monochromating unit 102.

Figure 2:
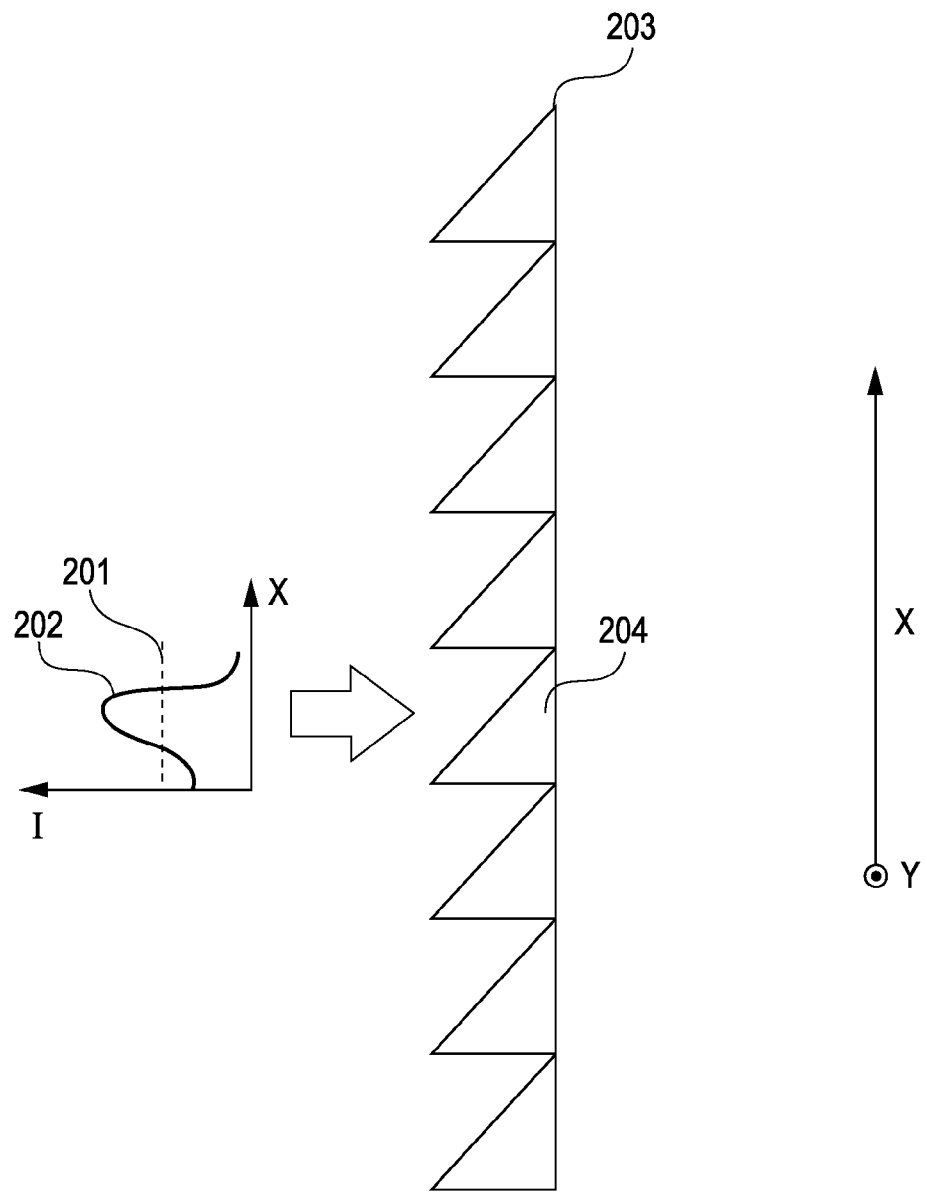
FIG. 2 is a schematic illustration of part of a scintillator array according to the first embodiment of the present invention.

The scintillator array 105 is described next. FIG. 2 is a schematic illustration of part of the scintillator array 105. The scintillator array 105 includes a plurality of scintillators 204 arranged therein. Each of the plurality of scintillators 204 has a shape of a triangle pole having a thickness increasing in a direction perpendicular to the incident X-ray (an −X direction). Such a structure of the scintillator 204 provides a fluorescence emission intensity gradient that causes the fluorescence emission intensity to vary in the X direction in accordance with an incident position of the X-ray. Note that the scintillator array 105 may be produced by processing a planar scintillator into the arranged scintillators 204.

In FIG. 2, a reference X-ray intensity distribution 201 is shown. The reference X-ray intensity distribution 201 is an intensity distribution of X-rays made incident on the scintillator 204 when the detection object 104 is not set. In addition, an X-ray intensity distribution 202 is shown. The X-ray intensity distribution 202 is a distribution of the intensities of X-rays that vary due to refraction, the intensities of the X-rays having been made incident on the scintillator 204 when the detection object 104 is set.

The detected fluorescence emission intensities are the same regardless of the intensity distribution of the X-rays made incident on any one pixel of the detector so long as the integration intensity is the same. However, if the scintillator 204 having a fluorescence emission intensity that varies in the X direction in accordance with an incident position of the X-ray is disposed, a change in X-ray intensity distribution due to the refraction of the X-ray caused by the detection object 104 can be converted into a change in fluorescence emission intensity distribution. For example, in FIG. 2, if a portion of the X-ray intensity distribution 202 having an increased intensity is shifted upward, the fluorescent intensity decreases. In contrast, if the portion of the X-ray intensity distribution 202 having an increased intensity is shifted downward, the fluorescent intensity increases. Accordingly, by comparing the fluorescence intensity detected when the detection object 104 is not set with that detected when the detection object 104 is set, even a slight refraction effect can be detected.

Since even a slight change in the fluorescence emission intensity distribution in a pixel of the detector 106 can be detected by using such a configuration, the distance between the detection object 104 and the detector 106 can be made small. Thus, the apparatus can be made compact in size. In addition, if a configuration in which the distance between the detection object 104 and the detector 106 is large is employed, a change in the fluorescence emission intensity distribution caused by a much slighter refraction effect can be detected. Furthermore, since this method uses the X-ray refraction effect in order to detect a phase shift, the need for X-rays having high coherency can be eliminated.

Figure 4:
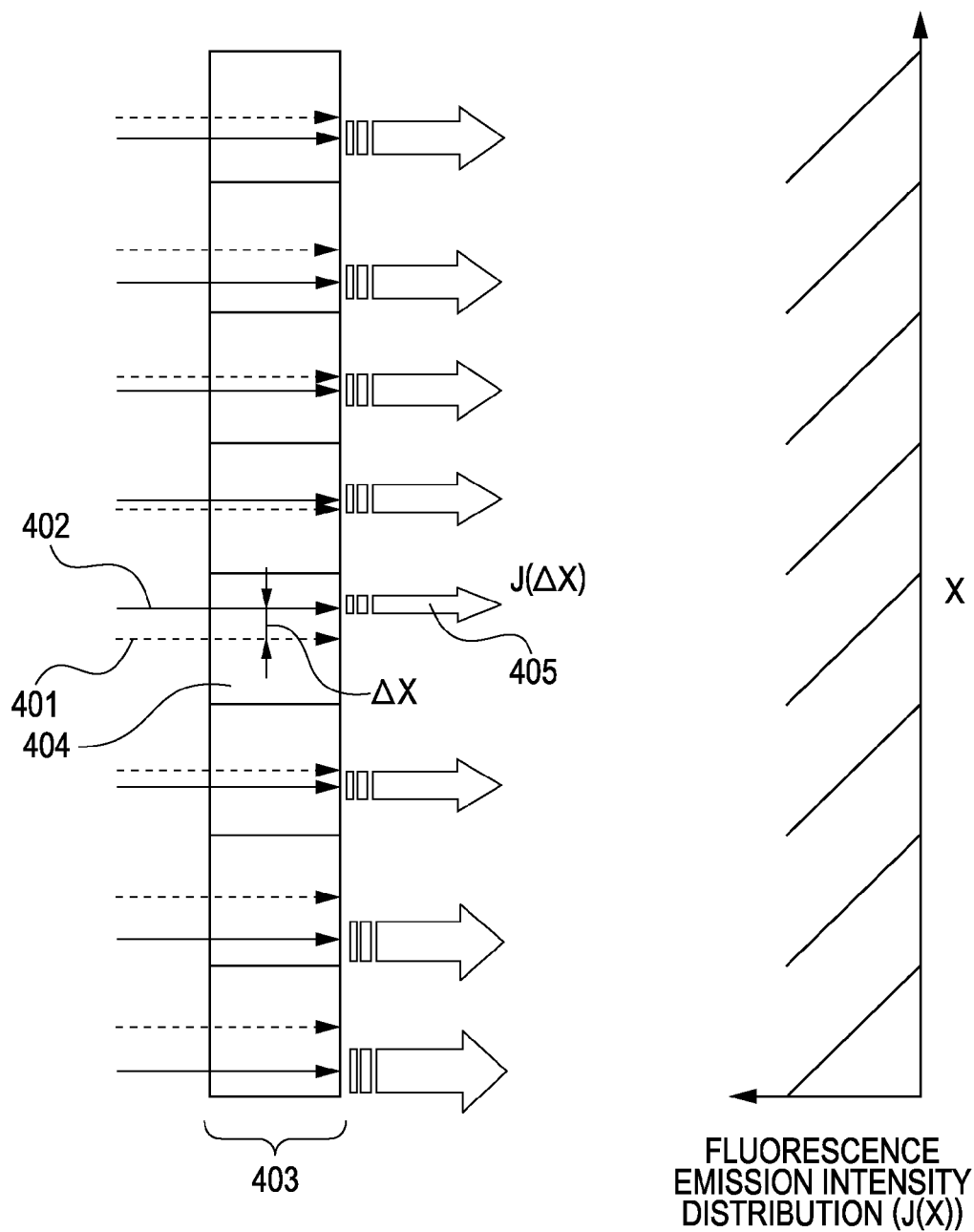
FIG. 4 is a schematic illustration of part of a scintillator array according to the second embodiment of the present invention.

While the above configuration has been described with reference to scintillators each having the same effective fluorescence emission intensity and having a shape that varies in a continuous manner, any scintillator that has a fluorescence emission intensity gradient such that the fluorescence emission intensity caused by the X-rays varies along a given direction can be used. For example, as shown in FIG. 4, a scintillator having a fluorescence emission intensity distribution that changes per unit area (the fluorescence emission intensity appearing when the same amount of X-rays is radiated) can be used in the X-ray imaging apparatus according to the present embodiment. Such a fluorescence emission intensity distribution can be obtained by changing the density distribution of a scintillator or the density distribution of the dopant in scintillator. Note that the fluorescence emission intensity distribution in the X direction as shown in FIG. 2 is also referred to as a "fluorescence emission intensity distribution in a direction perpendicular to the incident X-ray".

The fluorescence emission intensity gradient need not be continuous as shown in FIG. 2, but may be changed in a stepwise manner. For example, the shape of the scintillator may be changed in a stepwise manner, or the fluorescence emission intensity distribution of the scintillator may be changed in a stepwise manner.

In addition, the fluorescence emission intensity gradient of the scintillator may have a plurality of directions. For example, if a fluorescence emission intensity gradient in the X direction and a fluorescence emission intensity gradient in the Y direction are provided in a single scintillator, a phase gradient in directions of two dimensions can be measured. Examples of such a shape include a pyramid and a circular cone.

Alternatively, the phase gradients in directions of two dimensions can be measured by using a scintillator array in which a scintillator having a gradient in the X direction and a scintillator having a gradient in the Y direction are alternately arranged on the plane thereof.

Still alternatively, a scintillator array in which a scintillator having a gradient in the Y direction is stacked on a scintillator having a gradient in the X direction may be used. That is, a scintillator array having a gradient in the X direction may be disposed in the first layer, and a scintillator having a gradient in the Y direction may be disposed in the second layer. Yet still alternatively, in order to prevent an image from being blurred due to scattering X-rays output from the detection object 104, a grid used for X-ray machines may be provided between the scintillator array 105 and the detector 106.

Second Embodiment

Example of Configuration Including Separating Element

In a second embodiment of the present invention, an X-ray imaging apparatus and method that obtains a phase image from a phase shift in an X-ray are described. The second embodiment differs from the first embodiment in that the second embodiment includes an element that separates the X-ray.

Figure 3:
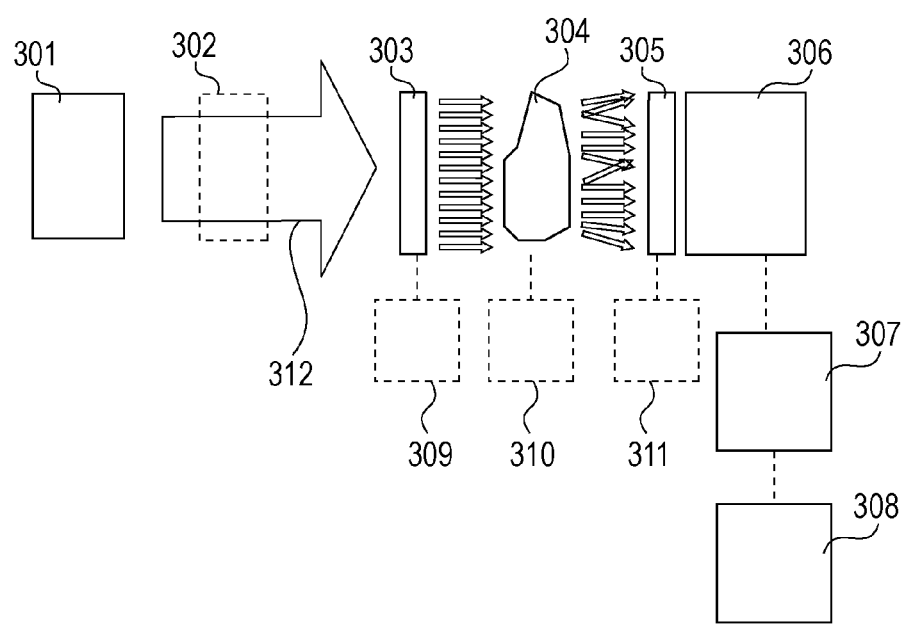
FIG. 3 illustrates an exemplary configuration of an X-ray imaging apparatus according to a second embodiment of the present invention.

FIG. 3 illustrates an X-ray imaging apparatus according to the present embodiment.

An X-ray 312 emitted from an X-ray source 301 is spatially separated by a separating element 303. That is, the X-ray that has passed through the separating element 303 forms a bundle of X-rays. The separating element 303 may have a slit-array shape having a line and a space or holes arranged two-dimensionally. In addition, the slit formed in the separating element 303 need not pass completely through a substrate. The material of the separating element 303 can be selected from Pt, Au, Pb, Ta, and W having a high X-ray absorption coefficient. Alternatively, an alloy of any of these materials can be used.

The period of the line and space of the X-ray separated by the separating element 303 is larger than or equal to the size of a pixel of a detector 306. That is, the size of a pixel of a detector 306 that detects the intensity of fluorescence emitted due to the X-ray is smaller than or equal to the period of the X-ray separated by the separating element 303.

The X-ray spatially separated by the separating element 303 is refracted by a detection object 304. Each of the refracted X-rays is made incident on a scintillator array 305. The X-ray is converted into a fluorescent by the scintillator array 305, and the intensity of each fluorescent is detected by the detector 306. The information regarding the fluorescent obtained by the detector 306 is mathematically processed by a computing unit 307, and the result is displayed on a display unit 308, such as a monitor.

In addition, it is desirable that the detector 306 be connected to the scintillator array 305 using optical components, such as a lens and a reflecting mirror. By combining such optical components with the scintillator array 305 and the detector 306, an X-ray that is transmitted through the scintillator array 305 and a scattered X-ray can be prevented from entering the detector 306. Thus, the S/N ratio of the detection data can be increased. Note that in order to accurately measure a change in the position of the X-ray caused by the presence of the detection object 304, a scintillator and a detector may be integrated together using a fiber plate.

In addition, moving units 309, 310, and 311 for moving the separating element 303, the detection object 304, and the scintillator array 305, respectively, are formed from, for example, stepping motors. Thus, the detection object 304 can be moved as needed. Accordingly, the image of a particular portion of the detection object 304 can be captured. Note that a monochromating unit 302, the detection object 304, the scintillator array 305, the detector 306, and a grid can be formed from those used in the first embodiment.

The scintillator array 305 is described in more detail below.

FIG. 4 illustrates a scintillator array according to the present embodiment. In FIG. 4, an optical path of a reference X-ray 401 (an X-ray traveling when the detection object 304 is not set) and an optical path of an X-ray 402 refracted by the detection object 304 are shown. In addition, a scintillator array 403, a scintillator 404, and fluorescence 405 emitted from the scintillator 404 due to the X-ray are shown.

The scintillator 404 is formed of a material that emits the fluorescence 405 when the scintillator 404 is irradiated with an X-ray. The scintillator 404 has a fluorescence emission intensity distribution of the fluorescence 405 that continuously changes in the X direction in the element shown in FIG. 4. The right section of FIG. 4 indicates that the scintillators 404 have a continuous fluorescence emission intensity distribution in the X direction.

For example, NaI (Tl doped), CsI (Tl or Na doped), LSO (Ce doped), YAP (Ce doped), or GSO (Ce doped) may be used as the light emitting material. By changing the density of the fluorescence emitting material of the scintillator 404, a fluorescence emission intensity distribution having a gradient can be provided. Alternatively, by changing an amount of dopant that contributes to fluorescence emission, a fluorescence emission intensity gradient can be provided. In this way, as shown in FIG. 4, the fluorescence emission intensity of the fluorescence 405 (J(X)) with respect to the incident position of the X-ray can be generated.

If the fluorescence emission intensity gradient of the scintillator 404 is known, a change in the position of the X-ray (ΔX) caused by refraction can be computed using a relationship between the fluorescence intensities relating to the reference X-ray 401 and the X-ray 402.

In order to compute a change in the position (ΔX), a data table indicating a correspondence between an incident position (X) of the X-ray on the scintillator 404 and the fluorescence emission intensity (J(X)) may be prestored in the computing unit 307 or a storage unit. Thereafter, a change in the position (ΔX) may be computed using the measured fluorescence intensity. Such a data table can be generated from data acquired by scanning the separating element 303 or the scintillator array 305 when the detection object 304 is not set. That is changing the position of the X-ray incident on the scintillator 404. When generating the data table, the fluorescence emission intensity at each position of the scintillator 404 may be detected using a single slit having a width that is the same as the slit width of the separating element 303 instead of moving the separating element 303.

Figure 5:
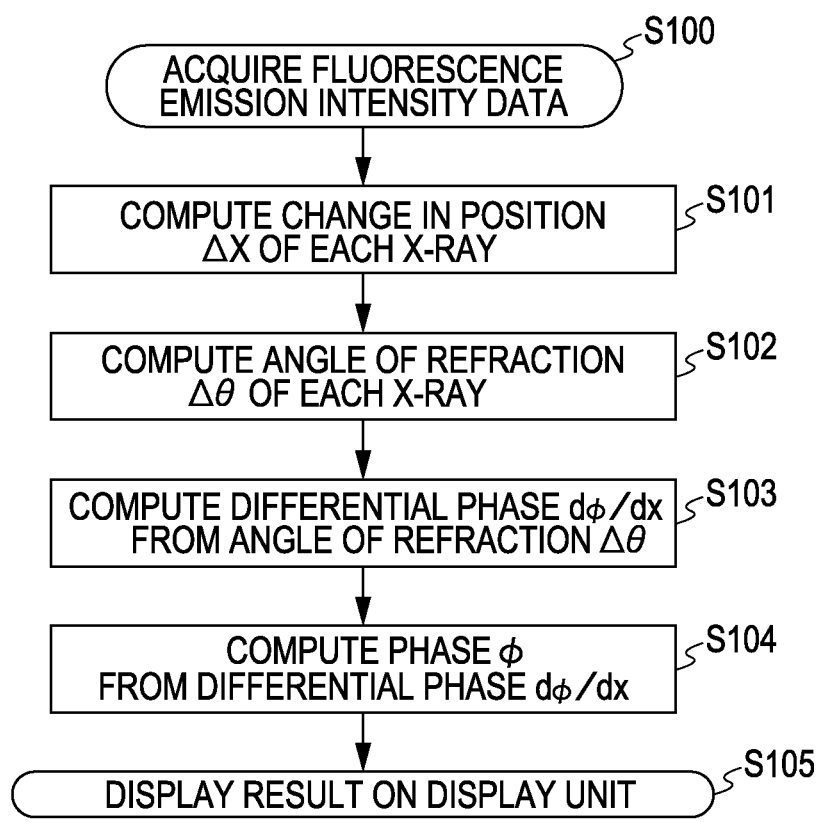
FIG. 5 is a flowchart of a computation process according to the second embodiment of the present invention.

An exemplary method for use in computation performed by the computing unit 307 according to the present embodiment is described next. FIG. 5 is a flowchart of the computation process.

First, in step S100, the intensity information on the fluorescence emitted from the scintillator array 305 is acquired.

Subsequently, in step S101, a change in the position (ΔX) of each X-ray with respect to the reference X-ray 401 is computed using the intensity information on the fluorescence emitted due to each X-ray. For example, by referencing a pregenerated database of the fluorescence emission intensity (J(X)) at each position of the scintillator 404 and actually measured intensity information, a change in the position (ΔX) is computed.

In step S102, an angle of refraction (Δθ) of each X-ray is computed. The angle of refraction (Δθ) of each X-ray can be expressed using the change in the position (ΔX) and a distance Z between the detection object 304 and the scintillator array 305 as follows:

[Math. 1]

$$\Delta\theta = \tan^{-1}\left(\frac{\Delta X}{Z}\right) \quad (1)$$

In addition, a relationship between the angle of refraction (Δθ) and a differential phase (dφ/dx) is expressed as follows:

[Math. 2]

$$\frac{d\phi}{dx} = \frac{2\pi}{\lambda}\Delta\theta \quad (2)$$

where λ represents the wavelength of an X-ray (the effective wavelength when continuous X-rays are used).

In step S103, the differential phase (dφ/dx) of each X-ray is computed using equation (2). Thus, differential phase information can be obtained.

In step S104, the obtained differential phase (dφ/dx) is integrated with respect to the X direction. Thus, phase information (φ) is obtained. Note that in step S105, a differential phase image and a phase image obtained in this manner can be displayed on the display unit 308.

According to the above-described configuration, even a slight change in the position of an X-ray can be detected and, therefore, the distance between the detection object 304 and the detector 306 can be decreased. That is, the apparatus can be made compact in size as compared with the apparatus using a refraction contrast method described in PTL 1.

In addition, by using the separating element 303, an amount of the differential phase and an amount of the phase can be quantified. In contrast, if a configuration in which the distance between the detection object 304 and the detector 306 is set to be large, a change in the position of the X-ray caused by a much slighter refraction can be measured. Furthermore, since this method uses an X-ray refraction effect in order to detect a phase shift, the need for X-rays having high coherency can be eliminated.

Third Embodiment

In a third embodiment of the present invention, an X-ray imaging apparatus using a scintillator array that differs from that used in the second embodiment is described. However, according to the third embodiment, the basic configuration of the X-ray imaging apparatus is the same as that of the second embodiment shown in FIG. 3.

Figure 6:
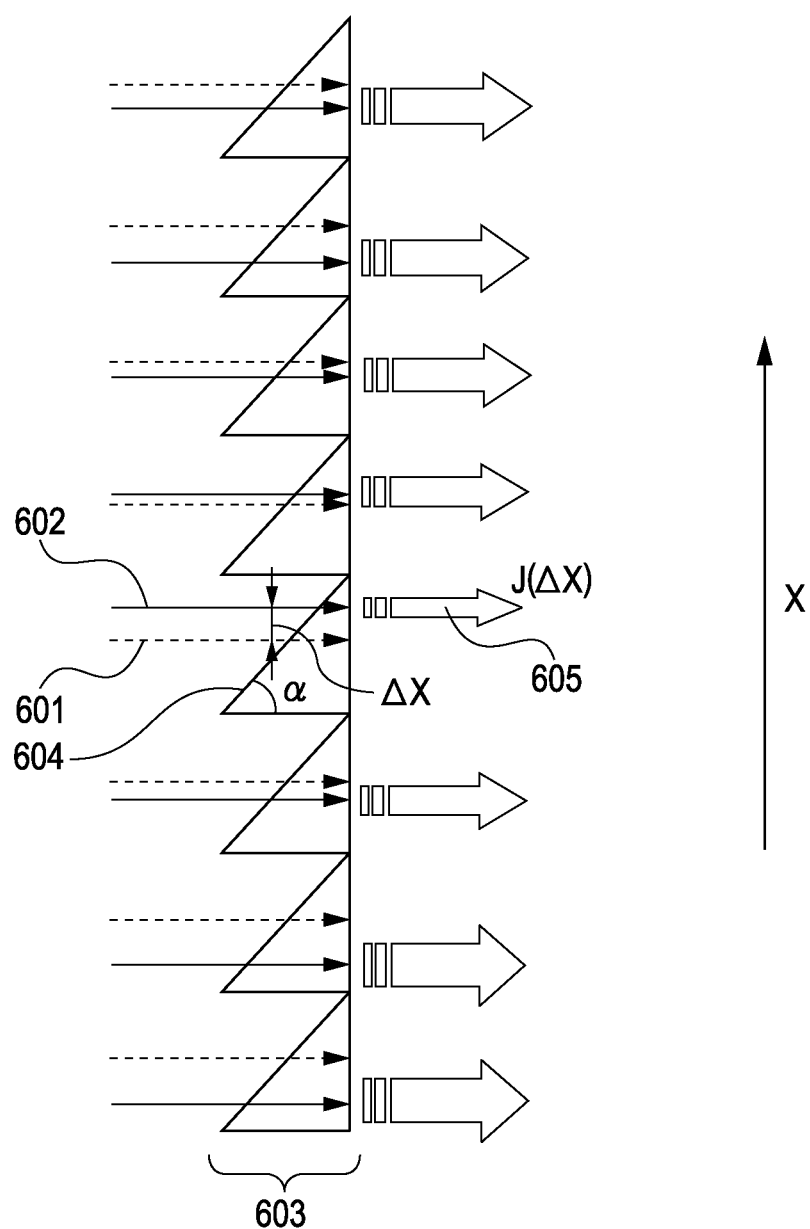
FIG. 6 is a schematic illustration of part of a scintillator array according to a third embodiment of the present invention.

FIG. 6 illustrates part of the scintillator array 305 shown in FIG. 3. The scintillator array 305 differs from the scintillator array 403 shown in FIG. 4.

In FIG. 6, an optical path of a reference X-ray 601 (an X-ray traveling when the detection object 304 is not set) and an optical path of an X-ray 602 refracted by the detection object 304 are shown. A scintillator array 603 includes scintillators 604, each having a shape of a triangle pole, arranged therein. The scintillators 604 are made of a material that emits fluorescence 605 when an X-ray is radiated.

It is desirable that the maximum thickness of each of the scintillators 604 be determined so that the employed X-rays can sufficiently pass through the scintillator 604. This is because if the traveling X-rays stop in the middle of the scintillator, the relationship between the intensity of the incident X-rays and the intensity of the fluorescence cannot be maintained and, therefore, an error may occur. Accordingly, in order to prevent the X-ray from directly entering the detector 306, it is desirable that an X-ray shielding material that allows the fluorescent to pass therethrough be disposed between the scintillator 604 and the detector 306 (refer to FIG. 3). For example, an optical fiber plate can be used as the X-ray shielding material. Since the scintillator 604 has a shape of a triangle pole, the fluorescence emission intensity changes in accordance with the incident position of the X-ray on the scintillator 604. When the reference X-ray 601 is made incident on the scintillator 604, the intensity J of the fluorescence 605 is expressed as follows:

$$J = k \cdot I_0 (1 - \exp(-\mu_{en} l_0)) \qquad (3)$$

where $I_0$ represents the intensity of the X-ray spatially separated by a separating element 203, $\mu_{en}$ represents the effective linear energy absorption coefficient of the material of the scintillator 604, $l_0$ represents the optical path length of the reference X-ray 601 in the scintillator 604, and k represents a coefficient. That is, equation (3) indicates that the X-rays other than those that have been transmitted through the scintillator 604 are converted to fluorescence.

In contrast, when the X-ray 602 irradiates the scintillator 604, a light intensity J' of the scintillator 604 is expressed as follows:

$$J' = k \cdot I_0 (1 - \exp(-\mu_{en} l)) \qquad (4)$$

where l represents the optical path length of the X-ray 602. The change in position ($\Delta X$) on the scintillator array 305 can be expressed using equations (3) and (4) and a vertex angle of the scintillator 604 ($\alpha$) as follows:

[Math. 3]

$$\Delta X = \frac{\tan \alpha}{\mu_{en}} \ln \left[ \frac{(1 - J'/kI_0)/}{(1 - J/kI_0)} \right] \qquad (5)$$

If the effect of absorption is not negligible, the transmittance of the X-ray as it travels through the detection object 304 can be computed using a scintillator that does not change the fluorescent intensity in accordance with a change in the position of the X-ray. For example, the shape of the scintillator 604 may be changed from a triangle pole to a square pole, and an image is captured. In this way, the transmittance of the X-ray can be obtained. In addition, since the linear energy absorption coefficient $\mu_{en}$ of the scintillator 604 is known, $kI_0$ can be computed by using measuring the fluorescence emission intensity J and using equation (3). Alternatively, the effective $kI_0$ and $\mu_{en}$ can be computed by scanning the scintillator array 603 in the X direction, obtaining the fluorescence emission intensity in accordance with a change in the position of the X-ray, and fitting equation (3) to the fluorescence emission intensity.

That is, even a slight change in position caused by the refraction in the detection object 304 can be computed using a relationship between the fluorescence intensities of the reference X-ray 601 and the refracted X-ray 602. Alternatively, like the second embodiment, according to the present embodiment, a change in the position of the X-ray ($\Delta X$) can be computed using the fluorescence emission intensity of the fluorescent 605 and a data table generated by measuring the fluorescence emission intensity of the fluorescent 605 (J(X)) in advance.

By performing computation using the data obtained in the above-described manner in accordance with the flowchart shown in FIG. 5, the differential phase (d$\phi$/dx) and the phase ($\phi$) can be computed. Thereafter, the differential phase image and the phase image can be displayed on the display unit 308.

Through such a configuration, even a slight change in the position of the X-ray can be detected. Thus, a long distance between the detection object 304 and the detector 306 is not necessary. As a result, the apparatus can be made compact in size. In addition, by using the separating element 303, an amount of the differential phase and the amount of the phase can be quantified. In contrast, if a configuration in which the distance between the detection object 304 and the detector 306 is set to be large, a change in the position of the X-ray caused by a much slighter refraction can be measured. Furthermore, since this method uses an X-ray refraction effect in order to detect a phase shift, the need for X-rays having high coherency can be eliminated.

Fourth Embodiment

Computed Tomography

In a fourth embodiment of the present invention, an exemplary configuration of an apparatus that uses a computed tomography (CT) technique and obtains a three-dimensional phase distribution is described.

Figure 7:
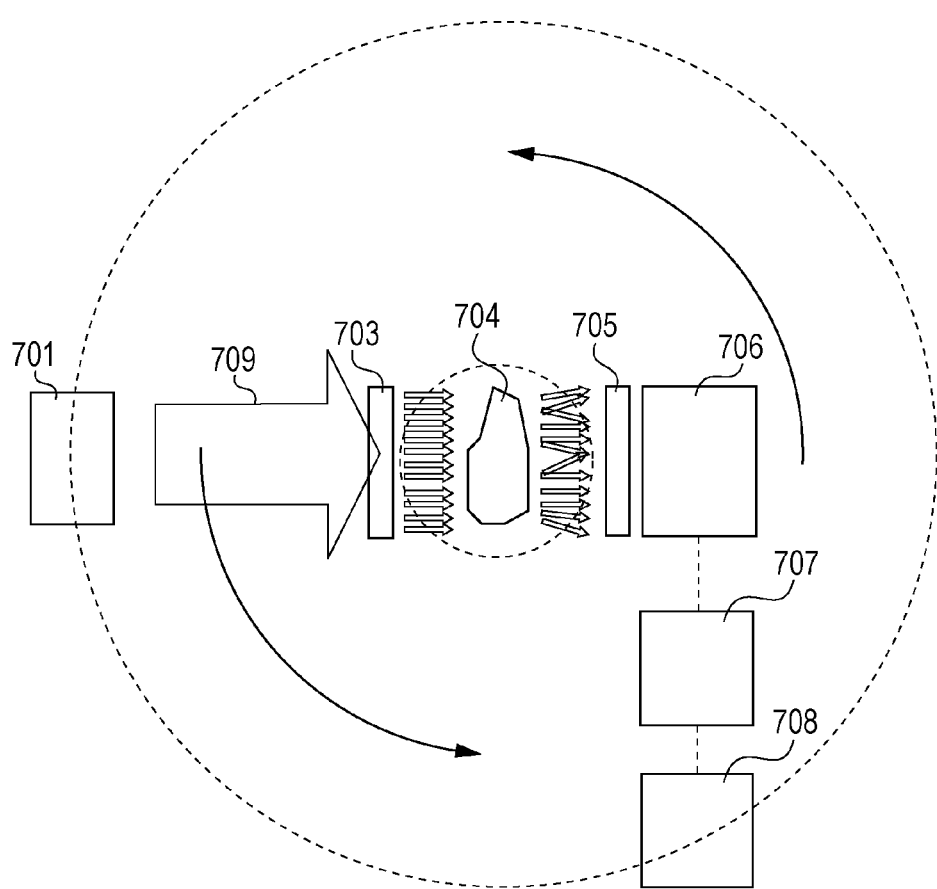
FIG. 7 illustrates computed tomography (CT) according to a fourth embodiment of the present embodiment.

FIG. 7 illustrates an exemplary configuration of a CT apparatus according to the present embodiment.

As shown in FIG. 7, the CT apparatus includes an X-ray source 701, a separating element 703, a detection object 704, a scintillator array 705, a detector 706, a computing unit 707, and a display unit 708.

In the CT apparatus according to the present embodiment, each of the X-ray source 701, the separating element 703, the scintillator array 705, and the detector 706 can be moved by a moving unit. Thus, the X-ray source 701, the separating element 703, the scintillator array 705, and the detector 706 can be synchronously moved around the detection object 704.

An X-ray 709 is spatially separated by the separating element 703. The separated X-rays 710 are emitted to the detection object 704. A transmission X-ray 711 is made incident on the scintillator array 705. By using the scintillator array 705, a slight change in the position of the separated X-ray caused by refraction in the detection object 704 can be obtained. The X-ray is converted into a fluorescent by the scintillator array 705. The fluorescence that has been emitted from the scintillator array 705 is detected by the detector 706. An image of the fluorescence is captured while synchronously moving the separating element 703, the scintillator array 705, and the detector 706 around the detection object 704. Thus, the projection data of the detection object 704 can be obtained. Alternatively, the separating element 703, the scintillator array 705, and the detector 706 may be fixed, and the detection object 704 may be rotated. Thus, projection data can be obtained.

Figure 8:
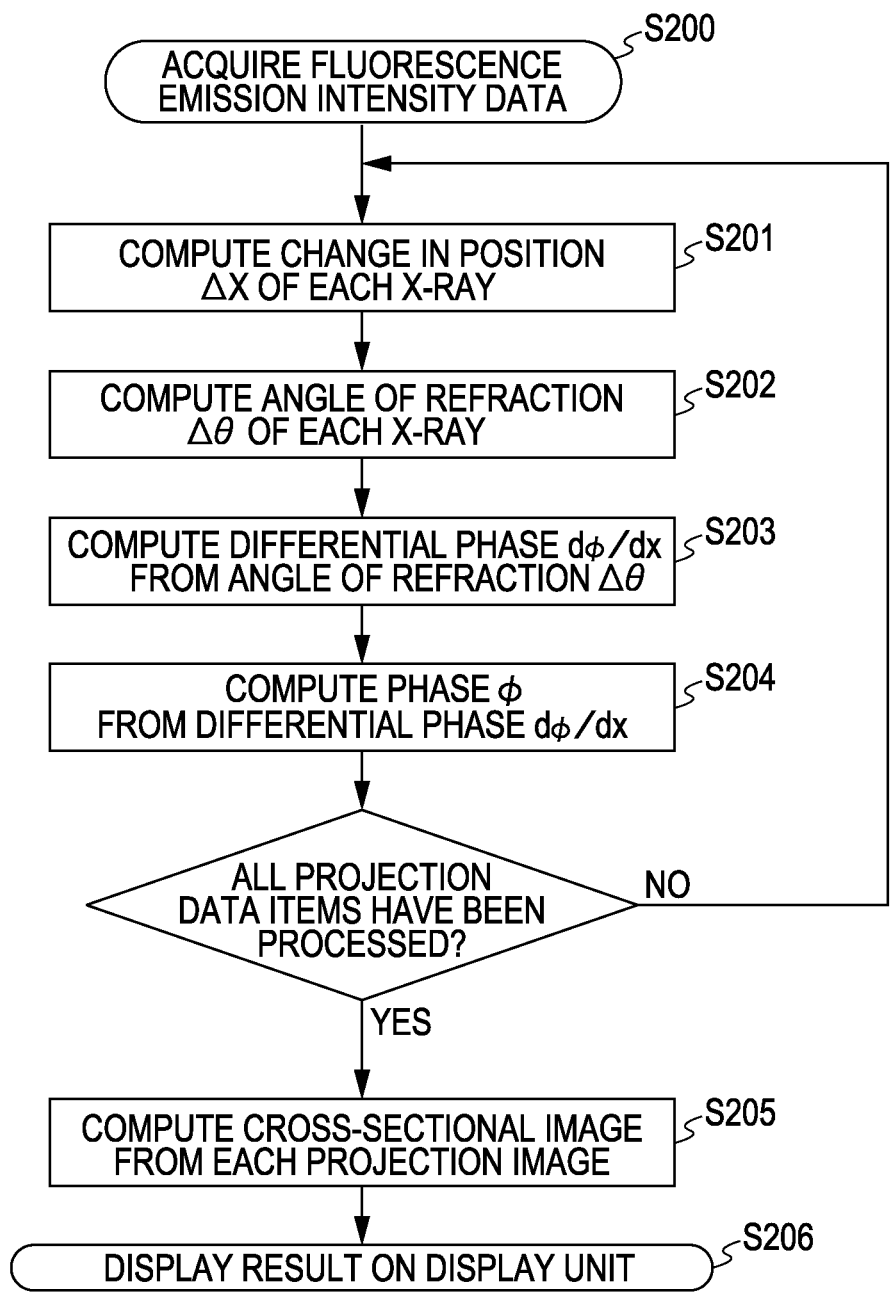
FIG. 8 is a flowchart of a computation process according to the fourth embodiment of the present embodiment.

A method for performing computation according to the present embodiment is described next. FIG. 8 is a flowchart of the computation process. First, in step S200, the fluorescence emission intensity information from the scintillator array 705 is acquired. Subsequently, in step S201, a change in the position ($\Delta X$) of each X-ray with respect to the reference X-ray 401 is computed. In step S202, an angle of refraction ($\Delta \theta$) of each X-ray is computed using the change in the position ($\Delta X$) and a distance Z between the detection object 704 and the scintillator array 705. Thereafter, in step S203, the differential phase (d$\phi$/dx) of each X-ray is computed using the angle of refraction ($\Delta \theta$). In step S204, the obtained differential phase (d$\phi$/dx) is integrated with respect to the X direction. Thus, the phase information ($\phi$) is obtained. Steps S201 to S204 are repeated for all of the projection data items. Finally, in step S205, a cross-sectional image for the phase (φ) is computed from the phase images of all of the projection data items using an image reconstruction method for computed tomography (e.g., a filtered back projection method). Note that in step S206, a cross-sectional image of the phase image can be displayed on the display unit 708.

Through such a configuration, the apparatus can be made compact in size. In addition, since this apparatus uses an X-ray refraction effect, the need for X-rays having high coherency can be eliminated. Accordingly, by using this CT apparatus, a three-dimensional image of the detection object can be acquired non-destructively.

Fifth Embodiment

Scintillator Array A for Obtaining Absorption Information

In a fifth embodiment of the present invention, an apparatus and a method for obtaining a correct differential phase image and a correct phase image of a detection object having high absorption of an X-ray is described. According to the present embodiment, the basic configuration of the X-ray imaging apparatus is the same as that of the second embodiment shown in FIG. 3.

According to the present embodiment, a scintillator array includes a scintillator for detecting a change in the position of an X-ray caused by a refraction effect (a first scintillator) and a scintillator for detecting the intensity of a transmission X-ray caused by an absorption effect of the detection object (a second scintillator). The fluorescence emission intensity of the second scintillator is constant regardless of the incident position of the X-ray. Here, the absorption information regarding the detection object can be obtained with the fluorescence emission intensity being substantially constant regardless of the incident position. That is, the fluorescence emission intensity need not be strictly constant. By detecting the fluorescence emission intensity of the fluorescence emitted from the scintillator array, an absorption image, a differential phase image, and a phase image can be obtained. The apparatus and method are described in more detail below.

Figure 9:
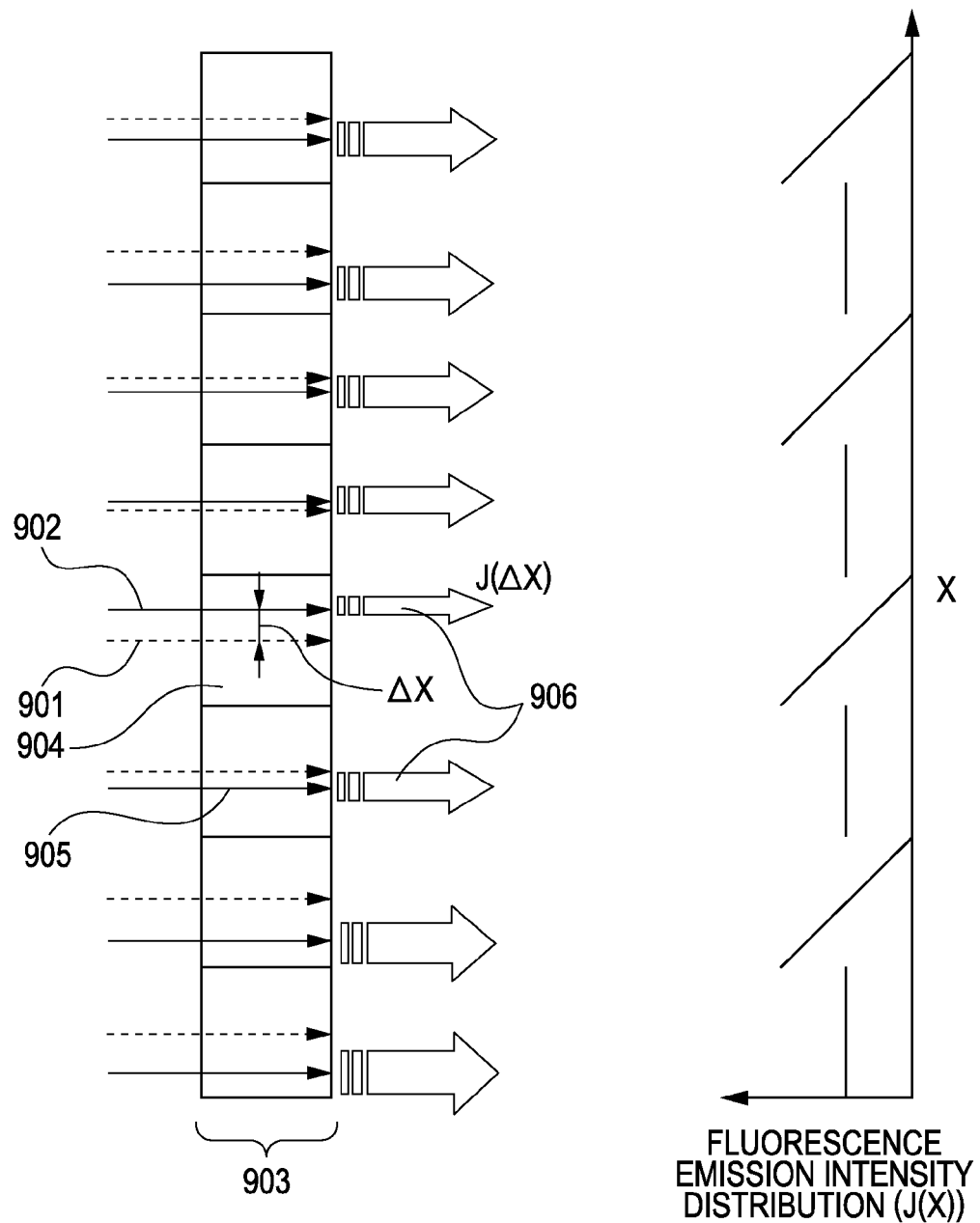
FIG. 9 is a schematic illustration of part of a scintillator array according to a fifth embodiment of the present invention.

FIG. 9 illustrates the scintillator array according to the present embodiment. In FIG. 9, an optical path of a reference X-ray 901 (an X-ray traveling when the detection object 304 is not set) and an optical path of an X-ray 902 refracted by the detection object 304 are shown. In addition, a scintillator array 903 includes scintillators 904 and 905 for converting a change in the position of the X-ray into the fluorescence emission intensity. The scintillators 904 and 905 are arranged at predetermined intervals in a plane. The scintillator 904 has a fluorescence emission intensity distribution that changes in the X direction in a continuous manner. However, the scintillator 905 has a fluorescence emission intensity distribution that does not change in the X direction. The scintillator 904 emits fluorescence 906 due to the X-ray. The right section of FIG. 9 indicates that the scintillators 904 have a continuous fluorescence emission intensity distribution in the X direction. Accordingly, the scintillator 904 emits fluorescence having an intensity in accordance with a change in the position of the X-ray refracted in the detection object 304 and the absorbed X-ray intensity. Note that, as an example, the scintillator 904 on the right side of FIG. 9 has a linear fluorescence emission intensity distribution. In addition, as in the second embodiment, an fluorescence emission intensity distribution (J(X)) of the scintillator 904 with respect to a change in the X-ray incident position (X) may be measured in advance.

In addition, as indicated by the right section of FIG. 9, the scintillator 905 has a uniform fluorescence emission intensity distribution. Thus, fluorescence corresponding to the intensity of the X-ray absorbed by the detection object 304 can be obtained. The fluorescence emission intensity distribution can be uniform in the element. However, it is desirable that control be performed so that the fluorescence emission intensity distribution is the same as the fluorescence emission intensity at the reference X-ray position of the scintillator 904. In addition, in order to prevent the X-ray from directly entering the detector 306, it is desirable that an X-ray shielding material that allows the fluorescent to pass therethrough be disposed between the detector 306 and each of the scintillators 904 and 905.

A change in the position of the X-ray with respect to the reference X-ray and the amount of absorption of the X-ray as it travels through the detection object can be computed by measuring the fluorescence emission intensities of the scintillators 904 and 905 and comparing with each other. This process is described below with reference to a schematic illustration of the fluorescence emission intensity of the scintillators in the X direction shown in FIG. 10 and a flowchart of the computation process shown in FIG. 11.

Figure 10:
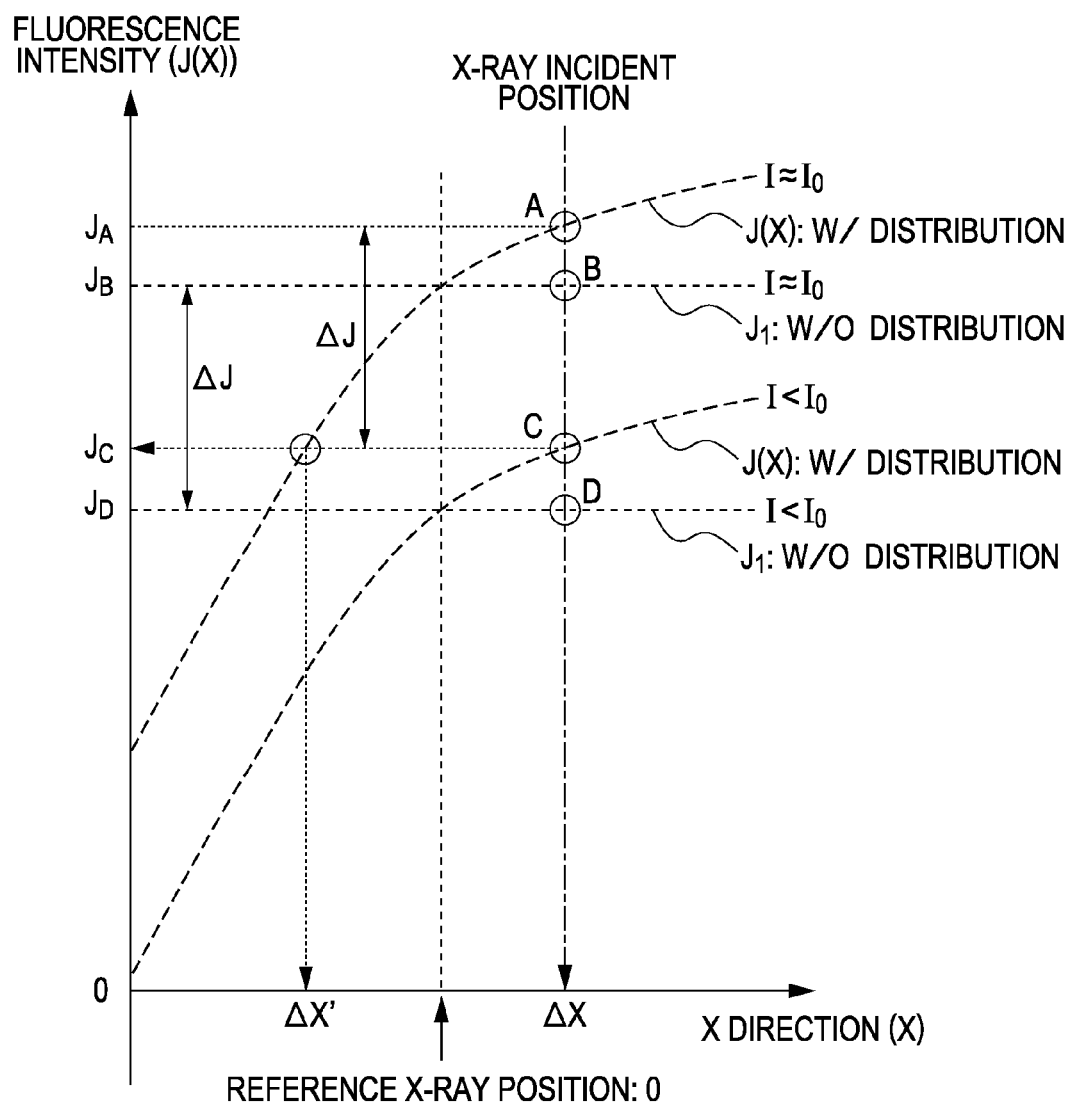
FIG. 10 is a schematic illustration of an effect of absorption by a detection object according to the fifth embodiment of the present invention.

When an X-ray is not absorbed by the detection object 304, an intensity I of the X-ray that passes through the detection object 304 is substantially the same as an intensity $I_0$ obtained before the X-ray transmits the detection object 304 (i.e., $I \approx I_0$). Accordingly, at a position of a change in the position due to the detection object 304 ($\Delta X$), a fluorescence emission intensity $J_A$ is obtained as indicated by a point A shown in FIG. 10. However, when an X-ray is absorbed by the detection object 304, the intensity I of the X-ray that passes through the detection object 304 is lower than the intensity $I_0$ (i.e., $I < I_0$). Accordingly, a fluorescence emission intensity $J_C$ is obtained as indicated by a point C shown in FIG. 10. In such a case, if the fluorescence emission intensity distribution J(X) obtained in advance is used, a change in the position $\Delta X'$ is obtained. That is, incorrect information is obtained. Therefore, it uses information of an neighbor scintillator having a uniform fluorescence emission intensity distribution ($J_1=J(0)$). If a fluorescence emission intensity $J_B$ obtained at a point B shown in FIG. 10 is measured in advance when the detection object is not set, a difference between the fluorescent emission intensities $\Delta J$ ($=J_B-J_D$) can be computed when absorption occurs. Since the fluorescence emission intensity $J_A=J_C+\Delta J$, a correct $\Delta X$ can be obtained by using J(X). Note that the difference in fluorescence emission intensity $\Delta J$ is the same as the amount of X-rays absorbed by the detection object 304.

Figure 11:
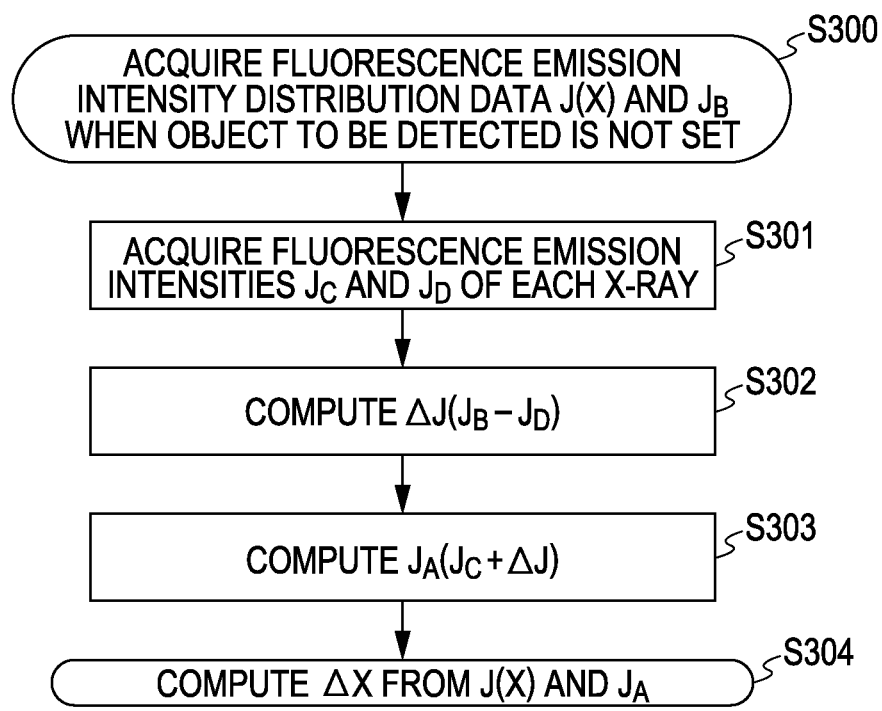
FIG. 11 is a flowchart of a computation process according to the fifth embodiment of the present invention.

A method for performing the computing process is described next with reference to the flowchart shown in FIG. 11. First, in step S300, the fluorescence emission intensity distribution J(X) of the scintillator having an fluorescence emission intensity distribution and the fluorescence emission intensity $J_B$ of the scintillator having no fluorescence emission intensity distribution are acquired in advance when the detection object is not set. Subsequently, in step S301, the detection object is measured so that the fluorescence emission intensity $J_C$ of the scintillator having a fluorescence emission intensity distribution and the fluorescence emission intensity $J_D$ of the scintillator having no fluorescence emission intensity distribution are acquired. Thereafter, in step S302, a difference between the fluorescence emission intensities $\Delta J$ ($=J_B-J_D$) that is the amount of absorption absorbed by the detection object is computed. In step S303, the fluorescence emission intensity $J_A$ ($=J_C+\Delta J$) subjected to correction using the amount of absorption absorbed by the detection object is computed. Finally, in step S304, $\Delta X$ is computed using the fluorescence emission intensity distribution J(X) of the scintillator having a fluorescence emission intensity distribution and $J_A$ obtained in step S303.

Thus, a change in the incident position of the X-ray 902 (ΔX) and an amount of absorption (the difference between the fluorescence emission intensities ΔJ) are obtained using the fluorescence emission intensities of the scintillators 904 and 905. Thereafter, a slight change in the index of refraction caused by the detection object 304 can be obtained.

It should be noted that a computation method is not limited to the above-described method. For example, the absorption information may be acquired from the fluorescence emission intensity obtained using the scintillator 905 and, subsequently, a change in position may be computed using this absorption information.

Note that when information on the fluorescence intensities in the regions of the scintillators 904 and 905 are obtained, the spatial resolution in the X direction is reduced by ½. Accordingly, in addition to the above-described measurement, by moving the scintillator array 305 in the X direction using the moving unit 311, the spatial resolution can be improved. Alternatively, by moving the detection object 304 in the X direction using the moving unit 310, the spatial resolution can be improved. In the above-described configuration, by using the scintillators 904 and 905, the X-ray absorption effect and the refraction effect can be obtained as independent information items.

By processing the data obtained in the above-described manner in accordance with the flowchart shown in FIG. 5, the differential phase (dφ/dx) and the phase (φ) are computed and, therefore, an absorption image, a differential phase image, and a phase image can be displayed on the display unit 308. Note that the absorption image, the differential phase image, and the phase image may be displayed on the screen at the same time or may be displayed separately.

The description of the present embodiment has been made with reference to the case in which the density distribution of the fluorescence emitting material or the dopant amount distribution is controlled. However, as described in Example 3 described below, the shape of a scintillator for measuring a change in position of the X-ray refracted may be, for example, a triangle pole, and the shape of a scintillator for measuring the absorption (the transmittance) may be a square pole. That is, a scintillator having a uniform thickness in a direction perpendicular to the incident X-ray may be used.

Sixth Embodiment

Scintillator Array B for Obtaining Absorption Information

As in the fifth embodiment, in a sixth embodiment of the present invention, an apparatus and a method for obtaining a correct differential phase image and a correct phase image of even a detection object having high absorption of an X-ray are described. According to the present embodiment, the basic configuration of the X-ray imaging apparatus is the same as that of the second embodiment illustrated in FIG. 3.

A scintillator array according to the present embodiment is characterized in that a change in the fluorescence emission intensity or an increasing and decreasing tendency of a scintillator with respect to the moving direction of the incident X-ray differs that of the neighboring scintillator. For example, the scintillator array is configured so that the fluorescence emission intensity of the first scintillator increases while the fluorescence emission intensity of the second scintillator decreases when the incident position of an X-ray is changed.

By using such scintillators, the absorption information and the phase information can be acquired independently. Thereafter, by using the acquired absorption information, more accurate differential phase image or phase image can be obtained. The scintillator array is described in more detail below.

Figure 12:
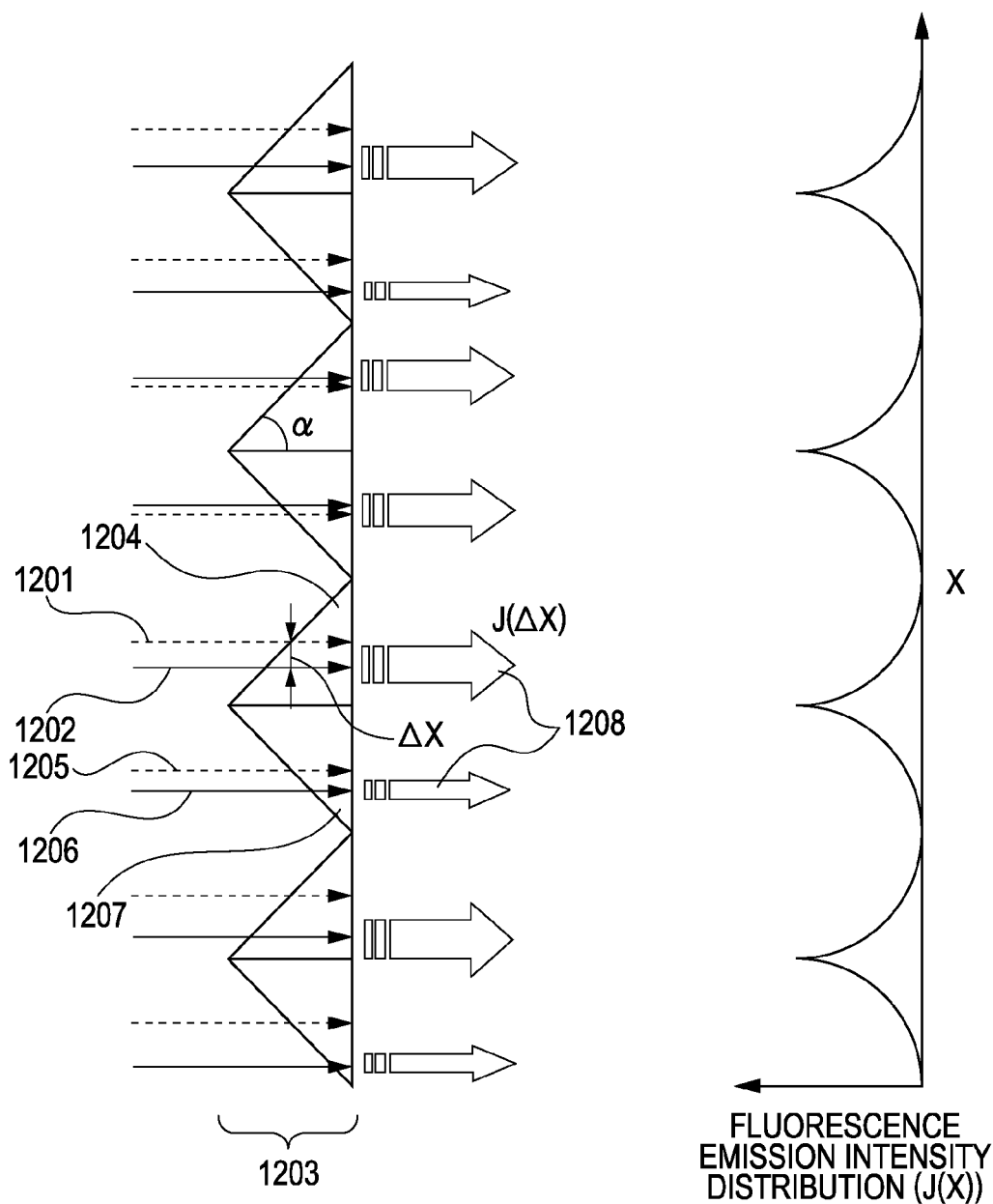
FIG. 12 is a schematic illustration of part of a scintillator array according to a sixth embodiment of the present invention.

FIG. 12 illustrates the scintillator array according to the present embodiment. In FIG. 12, the optical paths of reference X-rays 1201 and 1205 (reference X-rays when the detection object 304 is not set), the optical paths of X-rays 1202 and 1206 refracted in the detection object 304, a scintillator array 1203, and scintillators 1204 and 1207 periodically arranged in the scintillator array 1203 are shown. Each of the scintillators 1204 and 1207 has a shape of a triangle pole. Fluorescence 1208 is emitted from the scintillators 1204 and 1207 due to the X-rays.

As schematically shown in the right section of FIG. 12, the scintillators 1204 and 1207 have a fluorescence emission intensity gradient in the X direction, which is perpendicular to the incident direction of the X-rays.

Among the scintillators 1204 and 1207, the one having a longer optical path emits fluorescence. In addition, the tendencies of a change in fluorescence emission intensity distribution of the scintillators 1204 and 1207 are opposite to each other. Note that an X-ray shielding material that allows fluorescent to pass therethrough may be disposed between the detector 306 and each of the scintillators 1204 and 1207.

Let $\Delta X_1$ denote a change in the position of the refracted X-ray in the scintillator 1204, $J'_1$ denote the fluorescence emission intensity of the scintillator 1204, $\Delta X_2$ denote a change in the position of the refracted X-ray in the scintillator 1207, and $J'_2$ denote the fluorescence emission intensity of the scintillator 1207. In this case, since each of the fluorescence emission intensity distributions (J(X)) of the neighboring scintillators is symmetrical, the changes in the position of the X-ray for the fluorescence emission intensity have the following relationship:

$$\Delta X_1 = -\Delta X_2 \quad (6)$$

In addition, $J'_1$ and $J'_2$ can be expressed by using the transmittance A in the detection object 304 in equation (4), as follows:

$$J' = k \cdot I_0 A(1 - \exp(-\mu_{en} l)) \quad (7)$$

Furthermore, the change in the position ΔX can be expressed using equation (7) as follows:

[Math. 4]

$$\Delta X = \frac{\tan\alpha}{\mu_{en}} \ln\left[\frac{(1 - J'/kI_0 A)/}{(1 - J/kI_0)}\right] \quad (8)$$

By substituting $J'_1$ and $J'_2$ into $\Delta X_1$ and $\Delta X_2$ in equation (8) and using equation (6), A can be computed as follows:

[Math. 5]

$$A = [n(J'_1 + J'_2) + \sqrt{n^2(J'_1 + J'_2)^2 - 4(2nJ - J^2) * J'_1 * J'_2}]/2(2nJ - J^2) \quad (9)$$

where $n = kI_0$.

Here, since the linear energy absorption coefficient $\mu_{en}$ of the scintillator is known, n (i.e., $kI_0$) can be computed by measuring the fluorescence emission intensity J for the reference X-ray and using equation (3). Alternatively, by scanning the scintillator array 1203 in the X direction, acquiring the fluorescence emission intensity in accordance with a change in the position of an X-ray, and fitting equation (3) to the fluorescence emission intensity, effective $kI_0$ and $\mu_{en}$ can be computed.

Accordingly, the transmittance A can be computed by using the fluorescence emission intensity J obtained when the reference X-ray 1201 is made incident on the scintillator, the fluorescence emission intensity $J'_1$ of the fluorescence from the scintillator 1204, the fluorescence emission intensity $J'_2$ of the fluorescence from the scintillator 1207, and $kI_0$.

In addition, by substituting predetermined $\alpha$ and $\mu_{en}$ and $kI_0$, A, J', and J obtained through measurement into equation (8), the change in position ($\Delta X$) can be computed.

While the present embodiment has been described with reference to the fluorescence emission intensity distributions of the scintillators 1204 and 1207 being symmetrical, the fluorescence emission intensity distributions need not be symmetrical. As indicated by equation (6), if the relationship of a fluorescence emission intensity gradient between two scintillators is known, the X-ray transmittance and a change in position can be computed. That is, any neighboring scintillators having different changes in fluorescence emission intensity in the moving direction of the X-ray can be used. According to such a method, a change in position is obtained after the transmittance has been computed from the two scintillators. Therefore, a highly accurate differential phase image or phase image can be obtained even for a detection object that sufficiently absorbs X-rays.

Figure 13:
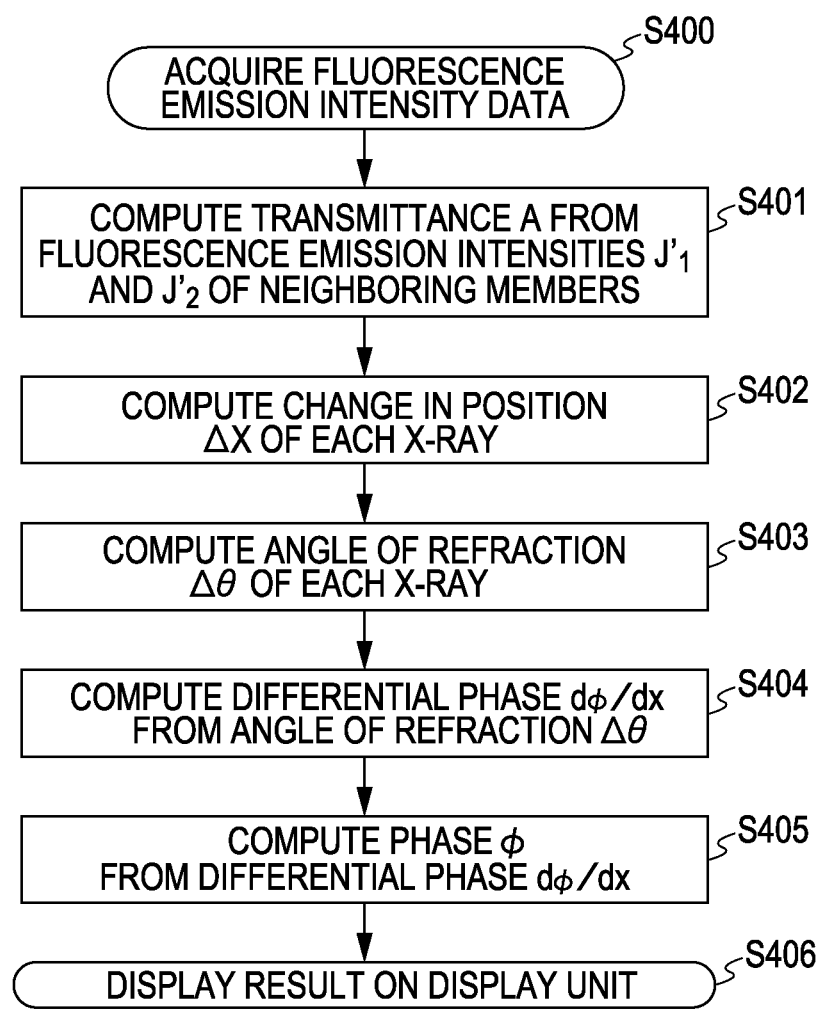
FIG. 13 is a flowchart of a computation process according to the sixth embodiment of the present invention.

The computing process is described next with reference to a flowchart shown in FIG. 13. First, in step S400, the fluorescence emission intensity data J' of the scintillator array is acquired. Subsequently, in step S401, a transmittance A is computed using fluorescence emission intensity $J'_1$ and $J'_2$ of neighboring scintillators obtained in step S400 and $kI_0$ obtained in advance when a detection object is not set. Subsequently, in step S402, a change in position ($\Delta X$) is computed by substituting, into equation (8), J' obtained in step S400, the transmittance A obtained in step S401, $\mu_{en}$, $kI_0$, and J obtained in advance when a detection object is not set, and $\alpha$. In step S403, the angle of refraction ($\Delta\theta$) of each X-ray is computed by substituting the change in position ($\Delta X$) and the distance between the detection object and the scintillator array (Z) into equation (1). In step S404, the differential phase ($d\phi/dx$) of each X-ray is computed by substituting $\Delta\theta$ computed in step S403 into equation (2). Thereafter, in step S405, the phase information ($\phi$) is computed by integrating the differential phase ($d\phi/dx$) computed in step S404 with respect to the X direction. Note that in step S406, an absorption image, a differential phase image, and a phase image obtained in this manner can be displayed on the display unit 308 as needed.

Note that when information on the fluorescence intensities in the scintillators 1204 and 1207 are obtained, the spatial resolution in the X direction is reduced by ½. Accordingly, in addition to the above-described measurement, by moving the scintillator array 1203 in the X direction using the moving unit 311 shown in FIG. 3, the spatial resolution can be improved. Alternatively, by moving the detection object 304 in the X direction using the moving unit 310, the spatial resolution can be improved.

As described above, by using the scintillators 1204 and 1207, the X-ray absorption effect and the refraction effect can be acquired independently. In addition, even a change in the position of the X-ray that is smaller than or equal to the pixel size of the detector 306 can be detected. Accordingly, the distance between the detection object and the detector can be reduced and, therefore, the apparatus can be made compact in size.

The present invention is described in more detail with reference to examples. However, the present invention is not limited thereto. Any type of a scintillator array, any shape of a scintillator, and any fluorescence emission intensity of a scintillator that are capable of converting a change in the position of an X-ray due to refraction into the fluorescent can be employed.

EXAMPLES

Examples of the present invention are described below.

Example 1

An exemplary configuration of an X-ray imaging apparatus of Example 1 according to the present invention is described next. This example corresponds to the above-described second embodiment.

Figure 14:
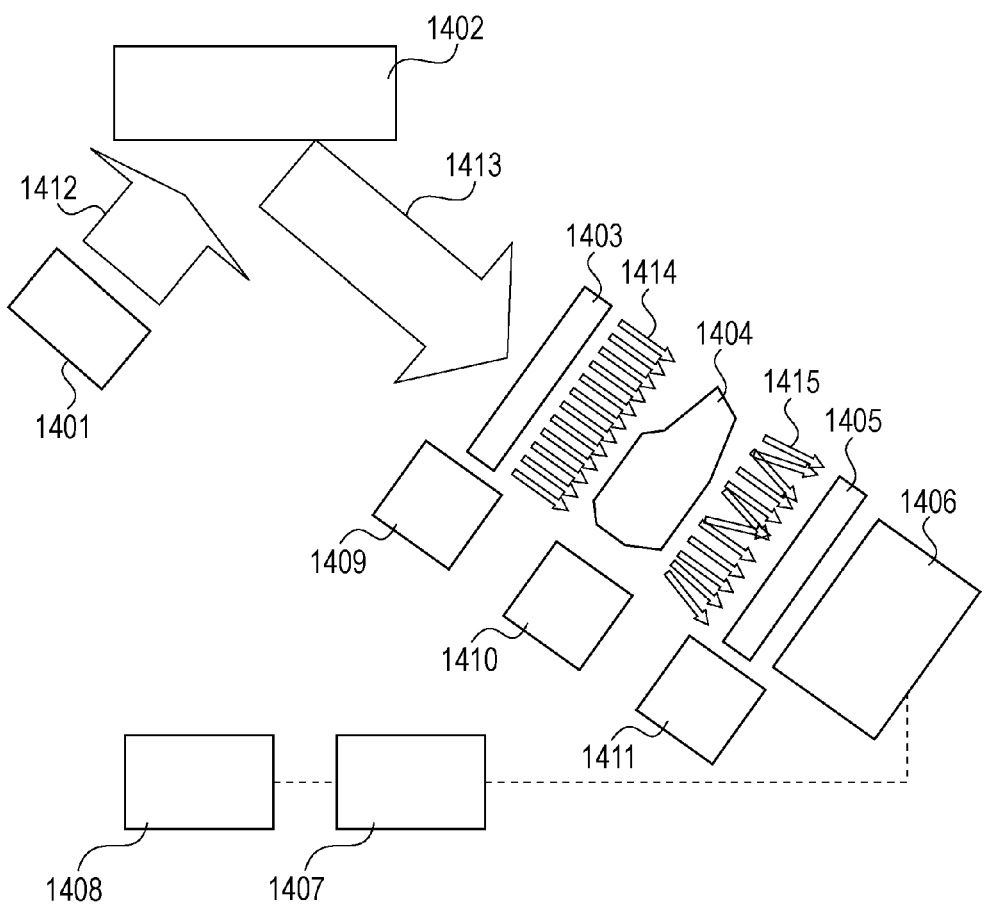
FIG. 14 illustrates an exemplary configuration of an X-ray imaging apparatus according to a first example of the present invention.

FIG. 14 illustrates an exemplary configuration of the present example. In FIG. 14, an X-ray source 1401, a monochromator 1402, a separating element 1403, a detection object 1404, a scintillator array 1405, a detector 1406, a computing unit 1407, and a display unit 1408 are shown. Note that the separating element 1403, the detection object 1404, and the scintillator array 1405 can be moved by moving units 1409, 1410, and 1411, respectively. Each of the moving units 1409, 1410, and 1411 includes a stepping motor.

An MO-target rotating anode X-ray generator unit shown as the X-ray source 1401 emits an X-ray 1412, and thus is used as an X-ray generator unit. A highly oriented Pyrolytic Graphite (HOPG) monochromator 1402 is used as an X-ray monochrometer. The monochromator 1402 extracts an MO characteristic X-ray. The X-ray monochromated 1413 by the monochromator 1402 is spatially separated by the separating element 1403, which is disposed at a position remote from the X-ray source 1401 by about 100 cm.

The separating element 1403 is made of W and has a thickness of 100 μm. The separating element 1403 has slits, each having a slit width of 40 μm, arranged therein. The period of the slits is 150 μm on the scintillator array 1405. Note that Au, Pb, Ta, or Pt is used for the material in stead of W.

The X-ray 1414 separated by the separating element 1403 is radiated to the detection object 1404. The X-ray 1415 transmitted through the detection object 1404 and is made incident on the scintillator array 1405 disposed at a position remote from the detection object 1404 by 50 cm.

The scintillator array 1405 has a structure in which CsI (Tl doped) scintillators each having a shape of a triangle pole with a vertex angle of about 80° are arranged. The period in the X direction is 150 μm. The scintillator array 1405 and the detector 1406 using a CCD having a pixel size of 25 μm couple by an optical fiber plate. The device including the integrated scintillator array 1405 and detector 1406 detects the fluorescence emission intensity.

The X-ray separated by the separating element 1403 is made incident upon the middle point of the triangle pole in the periodic direction. Note that in this example, for one X-ray separated by the separating element 1403, the fluorescence emission intensity values of six pixels in the periodic direction of the triangle pole are summed. The sum is defined as the fluorescence emission intensity of one scintillator.

A change in position ($\Delta X$) is obtained from the data table including the relationship between a detection intensity and a change in position ($\Delta X$) using the computing unit 1407. Thereafter, the index of refraction ($\Delta\theta$) is computed using equation (2). The differential phase is computed using the index of refraction (Δθ) and equation (3). Subsequently, a phase distribution image is obtained by integrating the obtained differential phase. The differential phase image or the phase image obtained by the computing unit 1407 is displayed on the display unit 1408 serving as a PC monitor.

Example 2

An exemplary configuration of an X-ray imaging apparatus of Example 2 according to the present invention is described next. This example corresponds to the above-described first embodiment.

Figure 15:
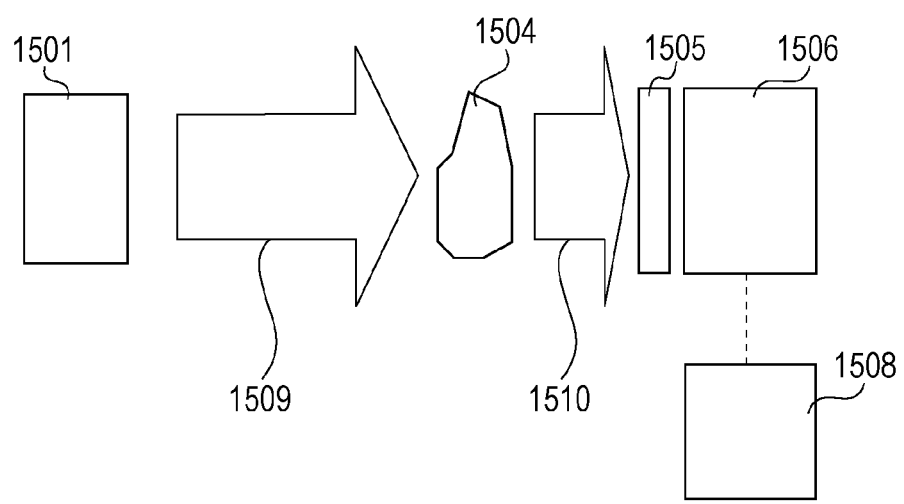
FIG. 15 illustrates an exemplary configuration of an X-ray imaging apparatus according to a second example of the present invention.

FIG. 15 illustrates an exemplary configuration of the present example. In FIG. 15, an X-ray source 1501, a detection object 1504, a scintillator array 1505, an X-ray detector 1506, and a display unit 1508 are shown.

In this example, an MO-target rotating anode X-ray generator unit shown as the X-ray source 1501 is used as an X-ray generator unit. An X-ray 1509 generated by the X-ray source 1501 is radiated to the detection object 1504 set at a position remote from the X-ray source 1501 by 100 cm. The X-ray is transmitted through the detection object 1504 and is made incident on the scintillator array 1505 disposed at a position remote from the detection object 1504 by 65 cm.

The scintillator array 1505 has a structure in which CsI (Tl doped) scintillators each having a shape of a triangle pole with a vertex angle of about 80° are arranged. The period in the X direction is 150 μm. The scintillator array 1505 and the detector 1506 using a CCD having a pixel size of 25 μm couple by an optical fiber plate. The device including the integrated scintillator array 1505 and detector 1506 detects the fluorescence emission intensity. A computed image obtained from an image captured when the detection object 1504 is not set is displayed on the display unit 1508 serving as a PC monitor.

Example 3

An exemplary configuration of an X-ray imaging apparatus of Example 3 according to the present invention is described next. This example corresponds to the above-described fifth embodiment.

The basic structure of this example is similar to that of Example 1 shown in FIG. 14. However, the configurations of the scintillator array 1405 and the computing unit 1407 differ from those of Example 1.

Figure 16:
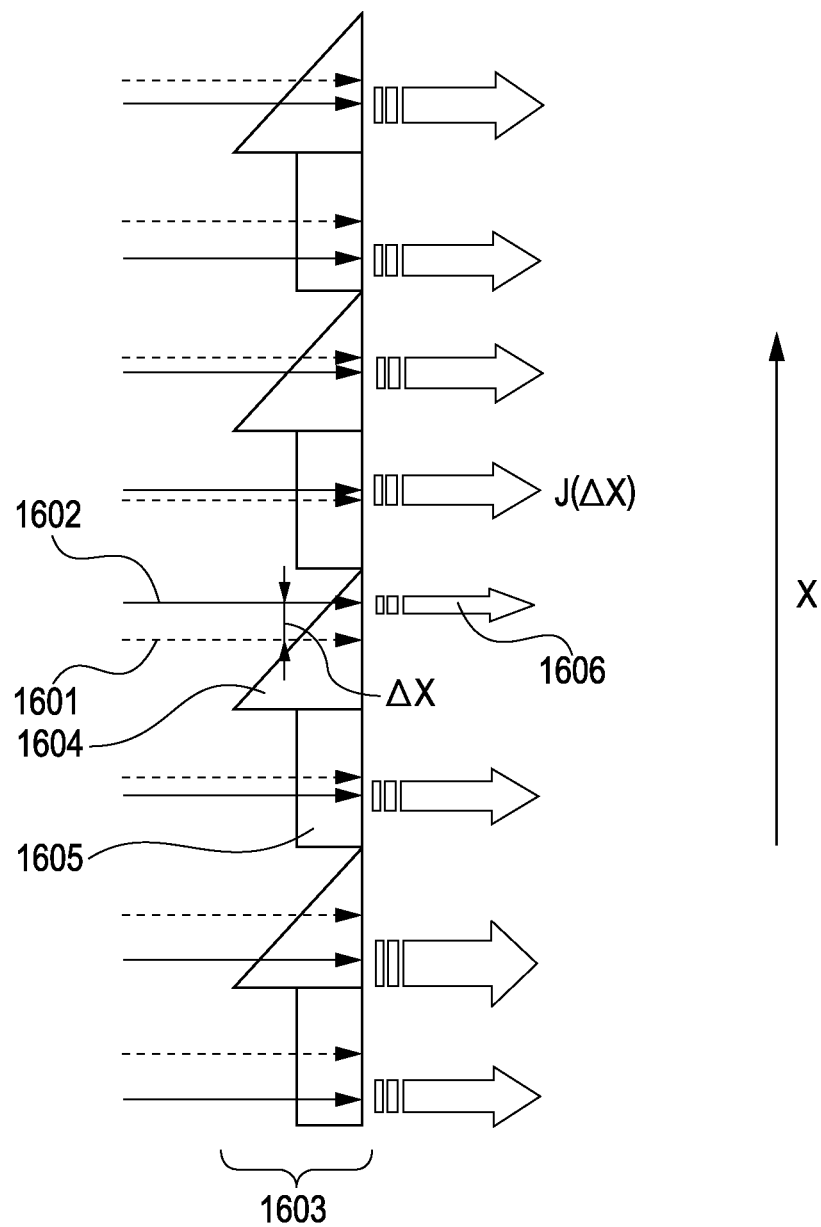
FIG. 16 is a schematic illustration of part of a scintillator array according to a third example of the present invention.

That is, the scintillator array 1405 of Example 3 is produced by processing CsI (Tl doped) formed on an optical fiber plate so that, as shown in FIG. 16, a rod having a shape of a triangle pole and a rod having a shape of a square pole are alternately arranged therein. The period of a scintillator 1604 having a shape of a triangle pole and a scintillator 1605 having a shape of a square pole is 150 μm. The vertex angle of the triangle pole of the scintillator 1604 is about 80°. The maximum thickness of the triangle pole is about 13 μm. The optical fiber plate including the scintillators 1604 and 1605 formed thereon and the detector 1406 including a CCD having a pixel size of 25 μm are integrated together. The device including the integrated scintillator array 1405 and detector 1406 detects the fluorescence emission intensity.

The X-ray separated by the separating element 1403 is made incident at the middle point of the corresponding scintillator in the periodic direction.

The detector 1406 serving as a detector disposed immediately downstream of the scintillator array 1405 detects the intensity of fluorescence induced by the X-ray. Note that in this example, for one X-ray separated by the separating element 1403, the fluorescence emission intensity values of six pixels in the periodic direction of the triangle pole are summed. The sum is defined as the fluorescence emission intensity of one scintillator. Thereafter, the scintillator array 1405 is moved in the periodic direction of the triangle pole and square pole by 150 μm (one period) using the moving unit 1411. Subsequently, measurement is performed in the same manner. Through the two measurements, the fluorescence emission intensity of the scintillator having a triangle pole and a square pole induced by the X-ray that has been transmitted through the detection object 704 can be obtained.

Using the computing unit 1407, an amount of absorption (ΔJ) and a change in position (ΔX) are obtained from the data table regarding the fluorescence emission intensity (J(X)) and a change in position (ΔX) for the triangle pole measured in advance. Thereafter, the index of refraction (Δθ) is computed using the change in position (ΔX) and equation (2). The differential phase is computed using the index of refraction (Δθ) and equation (3). Subsequently, a phase image is obtained by integrating the obtained differential phase.

The X-ray absorption image, the X-ray differential phase image, and the X-ray phase image obtained by the computing unit 1407 are displayed on the display unit 1408 serving as a PC monitor as needed.

Example 4

An exemplary configuration of an X-ray imaging apparatus of Example 4 according to the present invention is described next. This example corresponds to the above-described sixth embodiment.

The basic structure of this example is similar to that of Examples 1 and 3 shown in FIG. 14. However, the configurations of the scintillator array 1405 and the computing unit 1407 differ from those of Examples 1 and 3.

As shown in FIG. 12, the scintillator array 1405 of Example 4 is produced by processing CsI (Tl doped) formed on an optical fiber plate so that rods each having a shape of a triangle pole and a slope opposite to that of the neighboring rod are alternately arranged therein. The period of a scintillator 1204 and a scintillator 1207 is 150 μm. The vertex angle of the triangle pole is about 80°. The optical fiber plate including the scintillators 1204 and 1207 formed thereon and a detector 1406 including a CCD having a pixel size of 25 μm are integrated together. The device including the integrated scintillator array 1405 and detector 1406 detects the fluorescence emission intensity. The X-ray separated by the separating element 1403 is made incident at the middle point of the corresponding scintillator in the periodic direction. The detector 1406 serving as a detector disposed immediately downstream of the scintillator array 1405 detects the intensity of fluorescence induced by the X-ray. Note that in this example, for one X-ray separated by the separating element 1403, the fluorescence emission intensity values of six pixels in the periodic direction of the scintillator are summed. The sum is defined as the fluorescence emission intensity of one scintillator.

Thereafter, the scintillator array 1405 is moved in the periodic direction of the triangle pole by 150 μm (one period) using the moving unit 1411. Subsequently, measurement is performed in the same manner. Through the two measurements, the fluorescence emission intensity of the scintillator induced by the X-ray that has been transmitted through the detection object 1404 can be obtained.

Using the computing unit 1407, a change in position (ΔX) and the transmittance A are computed from the fluorescence emission intensity of the scintillator having a shape of a triangle pole and measurement data (J(X)) obtained when the detection object 1404 is not set. Thereafter, the index of refraction (Δθ) is computed using equation (2). Subsequently, the differential phase is computed using the index of refraction (Δθ) and equation (3). A phase image is computed by integrating the obtained differential phase.

The X-ray absorption image, the X-ray differential phase image, and the X-ray phase image obtained by the computing unit 1407 are displayed on the display unit 1408 serving as a PC monitor as needed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-173452, filed Jul. 24, 2009, which is hereby incorporated by reference herein in its entirety.

REFERENCE SIGNS LIST

301 X-ray source
302 monochromating unit
303 separating element
304 detection object
305 scintillator array
306 detector
307 computing unit
308 display unit
309 moving unit
310 moving unit
311 moving unit

The invention claimed is:

1. An X-ray imaging apparatus for acquiring X-ray information of phase shift caused by a detection object, comprising:
   a separating element configured to spatially separate X-rays generated by an X-ray generator unit;
   a scintillator array including a first scintillator and a second scintillator, the separated X-rays separated by the separating element being made incident on the scintillator array; and
   a detector configured to detect an intensity of fluorescence emitted from the scintillator array,
   wherein the detector includes a first pixel configured to detect an intensity of fluorescence emitted from the first scintillator and a second pixel configured to detect an intensity of fluorescence emitted from the second scintillator, and
   wherein the first scintillator is configured such that an intensity of fluorescence emitted from the first scintillator which is detected by the first pixel varies in accordance with an incident position of the X-ray with respect to an X-direction, and the second scintillator is configured such that an intensity of fluorescence emitted from the second scintillator which is detected by the second pixel is constant in accordance with an incident position of the X-ray with respect to the X-direction.

2. The X-ray imaging apparatus according to claim 1, further comprising:
   a computing unit configured to compute one of a differential phase image and a phase image of the detection object using fluorescence emission intensity information detected by the detector.

3. The X-ray imaging apparatus according to claim 1, wherein the first scintillator has a thickness that continuously varies along the X-direction.

4. The X-ray imaging apparatus according to claim 1, wherein for the first scintillator, fluorescence emission intensity thereof per unit volume varies continuously along the X-direction.

5. The X-ray imaging apparatus according to claim 1, wherein the second scintillator has a uniform thickness in the X-direction, and
   wherein the second scintillator has a constant fluorescence emission intensity thereof per unit volume along the X-direction.

6. The X-ray imaging apparatus according to claim 1, wherein the first pixel and the second pixel are arranged on a same plane surface.

7. The X-ray imaging apparatus according to claim 1, wherein the first scintillator is configured such that an emission intensity which is detected by the first pixel monotonically increases or monotonically decreases in accordance with the incident position of the X-ray.

8. The X-ray imaging apparatus according to claim 7, wherein the first scintillator is configured such that an emission intensity varies in a stepwise fashion.

9. The X-ray imaging apparatus according to claim 1, wherein the separated X-ray is arranged in the X-direction and the first scintillator and the second scintillator are arranged in the X-direction.

10. The X-ray imaging apparatus according to claim 1,
    wherein the scintillator array includes a plurality of the first scintillators and a plurality of the second scintillators, and
    wherein the separated X-ray is arranged in the X-direction and the first scintillator and the second scintillator are alternately arranged in the X-direction.

11. An X-ray imaging apparatus for acquiring X-ray information of phase shift caused by a detection object, comprising:
    a separating element configured to spatially separate X-rays generated by an X-ray generator unit;
    a scintillator array including a first scintillator and another scintillator, the separated X-rays separated by the separating element being made incident on the scintillator array;
    a detector configured to detect an intensity of fluorescence emitted from the scintillator array, the detector including a first pixel configured to detect an intensity of fluorescence emitted from the first scintillator and another pixel configured to detect an intensity of fluorescence emitted from the another scintillator;
    a computing unit configured to compute one of a differential phase image and a phase image of the detection object using fluorescence emission intensity information detected by the detector,
    wherein the first scintillator is configured such that an intensity of fluorescence emitted from the first scintillator and detected by the first pixel varies in accordance with an incident position of the X-ray with respect to an X-direction, and the another scintillator is configured such that an intensity of fluorescence emitted from the another scintillator and detected by the another pixel varies in accordance with an incident position of the X-ray with respect to the X-direction,
    wherein, when the incident position of an X-ray with respect to the X-direction is changed by Δx, the variation of the intensity of fluorescence emitted from the first scintillator and detected by the first pixel is different from the variation of the intensity of fluorescence emitted from the another scintillator and detected by the another pixel, and wherein one of fluorescence emission intensity of the first scintillator and fluorescent emission intensity of the another scintillator increases or decreases with respect to the change of the incident X-ray in the X-direction by $\Delta x$, and the another one of the fluorescence emission intensity of the first scintillator and the fluorescent emission intensity of the another scintillator increases or decreases with respect to the change of the incident X-ray in the X-direction by $\Delta x$, wherein in a case where fluorescence emission intensities of the first scintillator and the another scintillator both increase or decrease the variation of the intensities are different, and wherein the computing unit computes a transmittance corresponding to one pixel using the intensity of fluorescence detected by the first pixel and the intensity of fluorescence detected by the another pixel.

12. The X-ray imaging apparatus according to claim 11, wherein the separated X-rays are arranged in the X-direction and the first scintillator and the another scintillator are arranged in the X-direction.

13. The X-ray imaging apparatus according to claim 11, wherein the first pixel and the another pixel are arranged on a same plane surface.

14. The X-ray imaging apparatus according to claim 11, wherein, when the incident position of an X-ray with respect to the X-direction is changed by $\Delta x$, the variation of the intensity of fluorescence emitted from the first scintillator and detected by the first pixel increases by a first amount and the variation of the intensity of fluorescence emitted from the another scintillator and detected by the another pixel increases by another amount different from the first amount.

15. The X-ray imaging apparatus according to claim 11, wherein, when the incident position of an X-ray with respect to the X-direction is changed by $\Delta x$, the first scintillator is configured such that an intensity of fluorescence emitted from the first scintillator and detected by the first pixel increases and the another scintillator is configured such that the intensity of fluorescence emitted from the another scintillator and detected by the another pixel decreases.

16. The X-ray imaging apparatus according to claim 11, wherein the first scintillator is configured such that an emission intensity emitted from the first scintillator and detected by the first pixel monotonically increases or monotonically decreases in accordance with the incident position of the X-ray, and wherein the another scintillator is configured such that an emission intensity emitted from the another scintillator and detected by the another pixel monotonically increases or monotonically decreases in accordance with the incident position of the X-ray.

17. The X-ray imaging apparatus according to claim 16, wherein each of the first scintillator and the another scintillator is configured such that the emission intensity which is detected by each of the first pixel and the another pixel varies in a stepwise fashion.

18. The X-ray imaging apparatus according to claim 11, wherein the scintillator array includes a plurality of the first scintillators and a plurality of the another scintillators, and wherein the separated X-ray is arranged in the X-direction and the first scintillator and the another scintillator are alternately arranged in the X-direction.

* * * * *